US010234423B2

(12) United States Patent
Clemmer et al.

(10) Patent No.: US 10,234,423 B2
(45) Date of Patent: *Mar. 19, 2019

(54) HYBRID ION MOBILITY SPECTROMETER

(71) Applicant: Indiana University Research and Technology Corporation, Indianapolis, IN (US)

(72) Inventors: David E. Clemmer, Bloomington, IN (US); Michael A. Ewing, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,478

(22) Filed: May 26, 2017

(65) Prior Publication Data

US 2017/0307565 A1    Oct. 26, 2017

Related U.S. Application Data

(63) Continuation-in-part of application No. 15/023,575, filed as application No. PCT/US2014/056970 on Sep. 23, 2014, now Pat. No. 9,683,965.

(Continued)

(51) Int. Cl.
*H01J 49/00* (2006.01)
*G01N 27/62* (2006.01)
(Continued)

(52) U.S. Cl.
CPC .......... *G01N 27/622* (2013.01); *H01J 49/022* (2013.01); *H01J 49/26* (2013.01); *H01J 49/443* (2013.01); *H01J 49/46* (2013.01)

(58) Field of Classification Search
CPC .... H01J 37/222; H01J 37/1474; H01J 37/244; H01J 37/28; H01J 2237/21; H01J 2237/2806
(Continued)

(56) References Cited

U.S. PATENT DOCUMENTS 9,683,965 B2 * 6/2017 Clemmer ............. G01N 27/622
2007/0278396 A1 12/2007 Wu
(Continued)

OTHER PUBLICATIONS

PCT Search Report and Written Opinion for PCT/US2014/056970, completed Jan. 8, 2015.

*Primary Examiner* — Nicole Ippolito
*Assistant Examiner* — Hanway Chang
(74) *Attorney, Agent, or Firm* — Barnes & Thornburg LLP

(57) ABSTRACT

A hybrid ion mobility spectrometer includes a single-pass drift tube having an ion inlet and an ion outlet, a multiple-pass drift tube having an ion inlet and an ion outlet each coupled to the single pass drift tube between the ion inlet and the ion outlet thereof, and at least one ion steering channel controllable to selectively pass ions traveling through the single-pass drift tube into the multiple-pass drift tube via the ion inlet of the multiple-pass drift tube and to selectively pass ions traveling through the multiple-pass drift tube into the single-pass drift tube via the ion outlet of the multiple-pass drift tube. The single-pass drift tube separates in time ions traveling therethrough according to a first function of ion mobility, and the multiple-pass drift tube separates in time ions traveling one or more times therethrough according to the first or a second function of ion mobility.

20 Claims, 15 Drawing Sheets

Related U.S. Application Data

(60) Provisional application No. 61/882,891, filed on Sep. 26, 2013.

(51) Int. Cl.
| | |
|---|---|
| *H01J 49/26* | (2006.01) |
| *H01J 49/44* | (2006.01) |
| *H01J 49/46* | (2006.01) |
| *H01J 49/02* | (2006.01) |

(58) Field of Classification Search
USPC .................. 250/281, 282, 286, 288, 290
See application file for complete search history.

(56) References Cited

U.S. PATENT DOCUMENTS

| | | |
|---|---|---|
| 2011/0198493 A1 | 8/2011 | Clemmer et al. |
| 2012/0153140 A1 | 6/2012 | Makarov |
| 2012/0273669 A1 | 11/2012 | Ivashin et al. |
| 2013/0161506 A1 | 6/2013 | Ugarov |

* cited by examiner

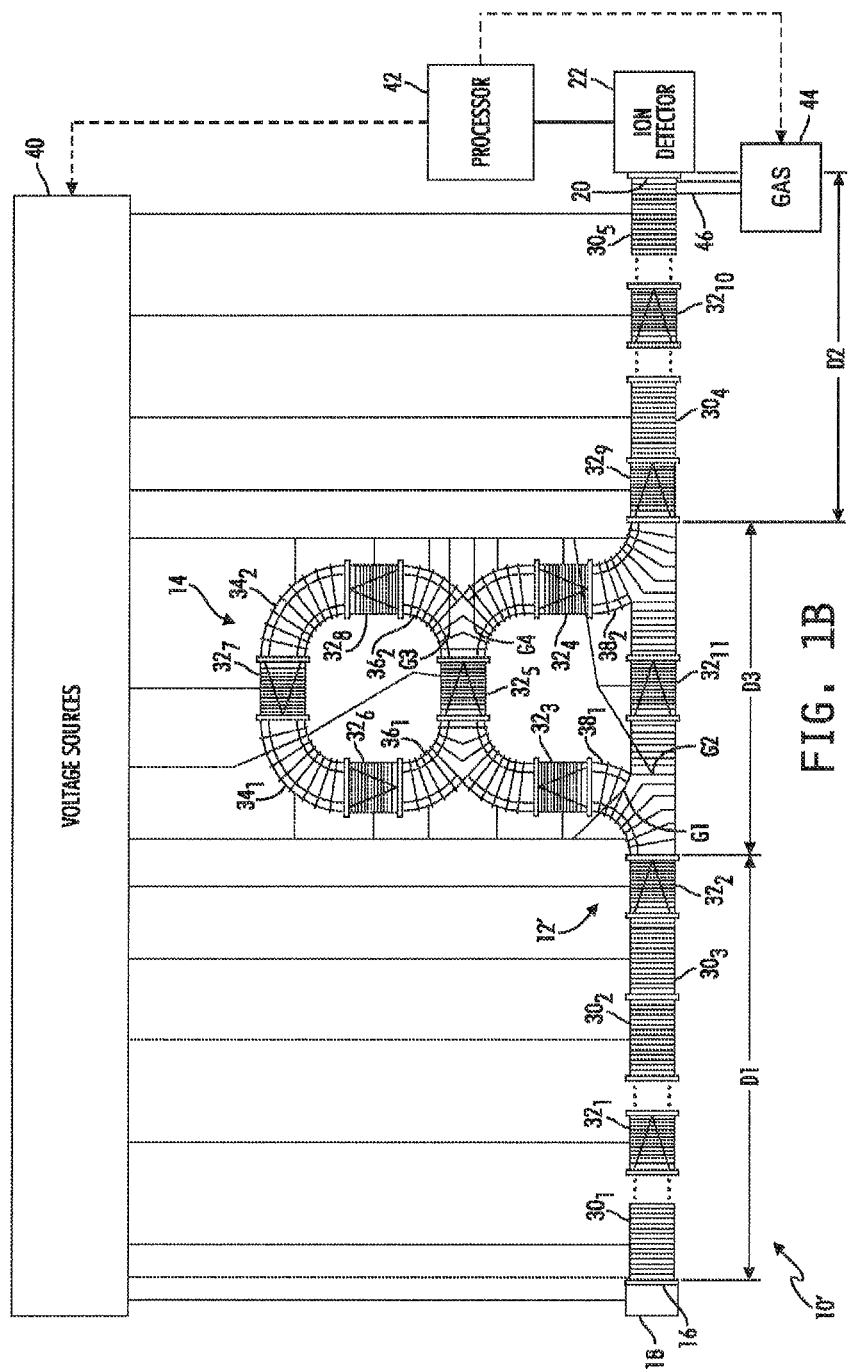

HYBRID ION MOBILITY SPECTROMETER

CROSS-REFERENCE TO RELATED APPLICATIONS

This is continuation-in-part of U.S. patent application Ser. No. 15/023,575, filed Mar. 21, 2016, which is a U.S. national phase of International Application No. PCT/US2014/056970, filed Sep. 23, 2014, which claims the benefit of, and priority to, U.S. Patent Application Ser. No. 61/882,891, filed Sep. 26, 2013, the disclosures of which are expressly incorporated herein by reference in their entireties.

GOVERNMENT RIGHTS

This invention was made with government support under GM090797 awarded by the National Institutes of Health. The United States Government has certain rights in the invention.

FIELD OF THE INVENTION

This disclosure relates generally to the field of spectrometry, and more specifically to instruments for separating ions in time as a function of ion mobility.

BACKGROUND

Ion mobility spectrometers are analytical instruments used to investigate properties of charged particles by separating the charged particles, i.e., ions, in time as a function of ion mobility. In the typical ion mobility spectrometers, an electric drift field is established in a drift tube filled with a buffer gas, and as the ions move through the drift tube under the influence of the electric drift field the ions collide with the buffer gas and separate as a function their collision cross-sections such that more compact conformers reach the end of the drift tube faster than less compact conformers. Known drift tubes may be so-called single-pass drift tubes, i.e., linear or non-linear drift tubes through which ions traverse only once between ion inlets and outlets thereof, or so-called multiple-pass drift tubes, i.e., linear or closed-path drift tubes through which ions may traverse multiple times before exit.

SUMMARY

The present invention may comprise one or more of the features recited in the attached claims, and/or one or more of the following features and combinations thereof. In one aspect, a hybrid ion mobility spectrometer may comprise a single-pass drift tube having an ion inlet at one end and an ion outlet at an opposite end, the single-pass drift tube configured to separate in time ions entering the ion inlet thereof and traveling therethrough according to a first function of ion mobility, a multiple-pass drift tube having an ion inlet and an ion outlet each coupled to the single pass drift tube between the ion inlet of the single-pass drift tube and the ion outlet of the single-pass drift tube, the multiple-pass drift tube configured to separate in time ions entering the ion inlet of the multiple-pass drift tube and traveling one or more times therethrough according to the first or a second function of ion mobility, and at least one ion steering channel controllable to selectively pass ions traveling through the single-pass drift tube into the multiple-pass drift tube via the ion inlet of the multiple-pass drift tube and to selectively pass ions traveling through the multiple-pass drift tube into the single-pass drift tube via the ion outlet of the multiple-pass drift tube.

In another aspect, a hybrid ion mobility spectrometer may comprise a single-pass drift tube configured to separate in time ions traveling axially therethrough in a first direction of ion travel according to a first function of ion mobility, a closed-path, multiple-pass drift tube configured to separate in time ions traveling axially therethrough one or more times in a second direction of ion travel according to the first or a second function of ion mobility, the second direction of ion travel different from the first direction of ion travel, and an ion steering channel disposed in-line with single-pass drift tube and in-line with the multiple-pass drift tube, the ion steering channel selectively controllable to steer ions traveling therein from the single-pass drift tube into the multiple-pass drift tube, the ion steering channel further selectively controllable to steer ions traveling therein from the multiple-pass drift tube into the single-pass drift tube.

BRIEF DESCRIPTION OF THE DRAWINGS

FIG. 1B is a simplified diagram of an alternate embodiment of a hybrid ion mobility spectrometer.

DESCRIPTION OF THE ILLUSTRATIVE EMBODIMENTS

For the purposes of promoting an understanding of the principles of the invention, reference will now be made to a number of illustrative embodiments shown in the attached drawing and specific language will be used to describe the same.

Figure 1A:
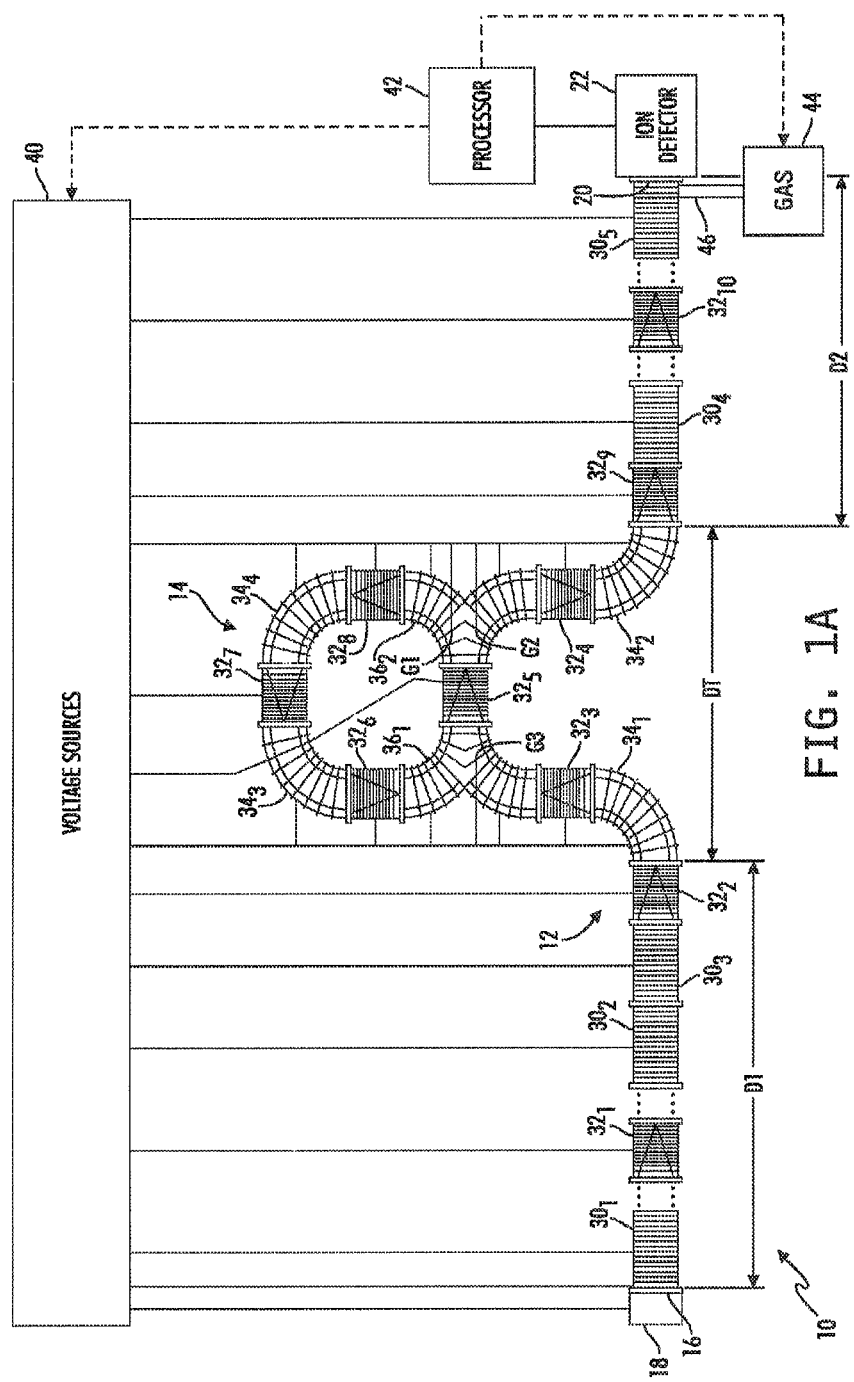
FIG. 1A is a simplified diagram of an embodiment of a hybrid ion mobility spectrometer.

Referring to FIG. 1A, a simplified diagram of an embodiment of a hybrid mobility spectrometer 10 is shown. The hybrid ion mobility spectrometer 10 illustratively includes a single-pass drift tube 12 through which ions can be separated in time according to a first function of ion mobility, and a multiple-pass drift tube 14, coupled to the single-pass drift tube 12 between an ion inlet 16 and an ion outlet 20 of the single-pass drift tube 12, through which ions can be separated in time according to a second function of ion mobility. The spectrometer 10 further illustratively includes a set of ion gates, e.g., G1-G3, each of which are controllable between open and closed positions, and the set of ion gates is illustratively controlled such that some or all of the ions traveling through the single-pass drift tube 12 may be selectively passed into the multiple-pass drift tube 14 via an ion inlet $36_1$ of the multiple-pass drift tube 14, and some or all of the ions traveling through the multiple-pass drift tube 14 may be selectively passed back into the single-pass drift tube 12 via an ion outlet $36_2$ of the multiple-pass drift tube 14, and the ions then exit the single-pass drift tube 12 via the ion outlet 20 thereof. In the embodiment illustrated in FIG. 1A, an ion source 18 is coupled to the ion inlet 16 of the single-pass drift tube 12, and an ion detector 22 is positioned to receive ions exiting the ion outlet 20 of the single-pass drift tube 12.

The foregoing configuration of the ion mobility spectrometer 10 provides for the ability to pass all or a subset of ions in the single-pass drift tube 12 to the multiple-pass drift tube 14 for additional and/or alternate separation before the ions exit the outlet 20 of the single-pass drift tube 12. Advantageously, because both drift tubes 12, 14 operate on ions generated from a single ion source 18 coupled to the ion inlet 16 of the single-pass drift tube 12, such additional and/or alternate separation may thus be carried out using ions from the same sample. In one specific operational mode of the hybrid ion mobility spectrometer 10 illustrated in FIG. 1A, for example, the set of ion gates, e.g., ion gates G1-G3, may be controlled such that ions generated by the ion source 18 are first confined to the single-pass drift tube 12, and electric fields within the single-pass drift tube 12 are controlled such that ions generated at the ion source 18 travel, i.e., drift, through only the single-pass drift tube 12 where they separate in time as a first function of ion mobility defined by the various structural dimensions and operating parameters of the single-pass drift tube 12. The resulting ion spectral information is then analyzed and if, for example, it is discovered that in the ion spectral information a subset, e.g., two or more, of ion intensity peaks in an ion mobility range of interest, e.g., in a particular range of drift times, are crowded together and cannot be satisfactorily resolved over the length of the single-pass drift tube 12, ions are then generated a second time, or are continuously generated without interruption, and the set of ion gates, e.g., ion gates G1-G3, is controlled in one embodiment to pass or divert ions traveling through the single-pass drift tube 12 that are within the ion mobility range of interest into the multiple-pass drift tube 14. The set of ion gates, e.g., ion gates G1-G3, is then controlled to confine the diverted ions within the multiple-pass drift tube 14 and electric fields within the multiple-pass drift tube 14 are controlled such that the diverted ions pass, i.e., drift, one or more times through, i.e., about, the multiple-pass drift tube 14 and separate in time according to a second function of ion mobility, which may or may not be the same as the first function of ion mobility, and which is defined by the structure and operating parameters of the multiple-pass drift tube 14, and the set of ion gates, e.g., ion gates G1-G3 may then be controlled to pass or divert some or all of the ions traveling through the multiple-pass drift tube 14 back into the single-pass drift tube 12 where they are then directed to the ion outlet 20 of the single-pass drift tube. In one alternate embodiment, the set of ion gates, e.g., ion gates G1-G3, may be controlled to pass or divert some or all of the ions traveling through the single-pass drift tube 12 into the multiple-pass drift tube 14, and the electric fields within the multiple-pass drift tube 14, along with the set of ion gates, e.g., ion gates G1-G3, may then controlled in a known manner to confine the diverted ions within the multiple-pass drift tube 14 so that the ions separate in time according to a second function of ion mobility in which only the diverted ions within the ion mobility range of interest pass one or more times through, i.e., about, the multiple-pass drift tube 14. The set of ion gates, e.g., ion gates G1-G3 may then be controlled to pass or divert some or all of the ions traveling through the multiple-pass drift tube 14 back into the single-pass drift tube 12 where they are then directed to the ion outlet 20 of the single-pass drift tube. In another alternate embodiment, the set of ion gates, e.g., ion gates G1-G3, may be controlled to pass or divert some or all of the ions traveling through the single-pass drift tube 12 into the multiple-pass drift tube 14, and the electric fields within the multiple-pass drift tube 14, along with the set of ion gates, e.g., ion gates G1-G3, may then controlled in a known manner to confine the diverted ions within the multiple-pass drift tube 14 so that the ions separate in time according to a second function of ion mobility, which may or may not be the same as the first function of ion mobility, and which is defined by the structure and operating parameters of the multiple-pass drift tube 14. The ion gates, e.g., ion gates G1-G3, may then be controlled to pass or divert some or all of the ions traveling through the multiple-pass drift tube 14 back into the single-pass drift tube 12, and one or more ion gates positioned within the drift tube section D2 may be controlled to pass through the ion outlet 20 only ions within the ion mobility range of interest.

In some embodiments, one or more of the ion gates in the set of ion gates, e.g., G1-G3, may be controlled to one or more intermediate positions between the open and closed positions. In such embodiments, and according to another specific operating mode of the hybrid ion mobility spectrometer 10 illustrated in FIG. 1A, for example, the set of ion gates, e.g., ion gates G1-G3, may be controlled to direct some of the ions traveling through the single-pass drift 12 into the multiple-pass drift tube 14 while also allowing others of the ions traveling through the single-pass drift tube 12 to travel completely through the single-pass drift tube 12, e.g., to and through the outlet 20 thereof. In such an operating mode, ions supplied by the single or common ion source 18 to the inlet 16 of the single-pass drift tube 12 thus travel in parallel through the single-pass drift tube 12 and the combination of the single-pass drift tube 12 and the multiple-pass drift tube 14, with some of the ions traveling directly through the single-pass drift tube 12 to and through the ion outlet 20 and others of the ions traveling through the single-pass drift tube 12, to and through the multiple-pass drift tube 14, then back to and through any remaining section(s) of the single-pass drift tube 12 and exiting the ion outlet 20 of the single-pass drift tube 12.

In any case, further details relating to various structural embodiments of the hybrid ion mobility spectrometer briefly described above and the foregoing operation thereof are described below and/or illustrated in the attached drawings, although it will be understood that other structural embodiments and operational modes of the hybrid ion mobility spectrometer illustrated and described herein will occur to those skilled in the art and that such other structural embodiments and operational modes are contemplated by this disclosure.

Referring now specifically to FIG. 1A, an embodiment of the hybrid ion mobility spectrometer 10 briefly described above is shown. As described above, the hybrid ion mobility spectrometer 10 includes an ion source 18 coupled to an ion inlet 16 defined at one end of a single-pass ion mobility spectrometer 12, and an ion outlet 20 is defined at an opposite end of the single-pass ion mobility spectrometer 12. A multiple-pass ion mobility spectrometer 14 is coupled to the single-pass ion mobility spectrometer 12 between the ion inlet 16 and the ion outlet 20 thereof such that ions may be selectively passed from the single-pass ion mobility spectrometer 12 to the multiple-pass ion mobility spectrometer 14 and vice versa. For purposes of this disclosure, the term "single-pass ion mobility spectrometer" means an ion mobility spectrometer, or portion thereof, through which ions pass a single time, and the term "multiple-pass ion mobility spectrometer" means an ion mobility spectrometer, or portion thereof, through which ions may pass multiple times. Neither such ion mobility spectrometer is limited to any particular shape or configuration, and the single-pass ion mobility spectrometer 12 and/or the multiple-pass ion mobility spectrometer 14 may be or include a linear, piece-wise-linear and/or non-linear drift tube.

In the illustrated embodiment, the ion outlet 20 of the single-pass ion mobility spectrometer 12 is coupled to an ion detector 22 which is configured to detect, in a conventional manner, ions exiting the ion outlet 20 of the single-pass ion mobility spectrometer 12. In alternate embodiments, one or more additional ion separation and/or ion analyzing apparatuses may be positioned between the ion outlet 20 of the single-pass ion mobility spectrometer 12 and the ion detector 22, and in any such alternate embodiment one or more ion detectors 22 may be coupled to or integral with any of the additional ion separation and/or ion analyzing apparatuses, alternatively to or in addition to the single-pass ion mobility spectrometer 12.

The ion source 18 may be any conventional ion source, examples of which include, but are not limited to, an electrospray ion source, a matrix-assisted laser desorption ion source (MALDI), or the like. Alternatively or additionally, the ion source 18 may include one or more conventional apparatuses to collect all or a subset of the generated ions (i.e., within a defined range of ion mobilities and/or within a defined range of ion mass-to-charge ratios) and/or to structurally modify, e.g., fragment and/or change the conformations of, some or all of the generated ions and/or to normalize or otherwise modify the charge states of one or more of the generated ions. Alternatively or additionally still, the ion source 18 may be or include one or more known apparatuses that separate ions and/or one or more isotopes thereof as a function of any molecular characteristic, e.g., ion mass-to-charge ratio, ion mobility, ion retention time, or the like.

In the embodiment illustrated in FIG. 1A, the single-pass ion mobility spectrometer 12 is made up of three cascaded drift tube sections; a first drift tube section D1 coupled to the ion source 18, a transition drift tube section DT coupled to the first drift tube section D1 and to the drift tube of the multiple-pass ion mobility spectrometer 14, and a second drift tube section D2 coupled to the transition drift tube section DT and, in the illustrated embodiment, to the ion detector 22. In one embodiment, the first drift tube section D1 is illustratively a linear drift tube section and includes a cascaded arrangement of any number, N, of conventional linear drift tube sub-sections $30_N$ (three such drift tube sub-sections $30_1$, $30_2$ and $30_3$ shown) and any number, M, of conventional linear drift tube funnels $32_M$ (two such drift tube funnels $32_1$ and $32_2$ shown), wherein a different drift tube funnel 32 may be interposed between any number of cascaded drift tube sub-sections 30. The second drift tube section D2 is likewise illustratively a linear drift tube section and may likewise include a cascaded arrangement of any number, Q, of conventional drift tube sections $30_Q$ (two such drift tube sub-sections $30_4$ and $30_5$ shown) and any number, R, of conventional drift tube funnels $32_R$ (two such drift tube funnels $32_9$ and $32_{10}$ shown), wherein a different drift tube funnel 32 may be interposed between any number of cascaded drift tube sub-sections 30. Alternatively, the second drift tube section D2 may include only a single drift tube sub-section 30 or drift tube funnel 32 which is coupled at one end to the transition drift tube section DT and defines the ion outlet 20 of the single-pass ion mobility spectrometer 12 at its opposite end. Alternatively still, the second drift tube section D2 may be omitted altogether and the ion outlet of the transition drift tube section DT may define the ion outlet 20 of the single-pass ion mobility spectrometer 12.

The drift tube sub-sections 30 and the drift tube funnels 32 illustrated in FIG. 1A are illustratively linear components in that each drift tube sub-section 30 and each drift tube funnel 32 defines a linear ion drift tube axis therethrough between an ion inlet and ion outlet thereof. The resulting drift tube sections D1 and D2 shown in FIG. 1A therefore likewise linear drift tube sections, it will be understood that either or both of the drift tube sections D1 and D2 may alternatively be piecewise linear or non-linear, or include one or more piecewise linear or non-linear subsections.

In any case, the one or more drift tube funnels 32 are illustratively controlled in a conventional manner to radially focus ions inwardly toward a central ion drift axis defined through the drift tube funnel 32 from an ion inlet to an ion outlet thereof. Additionally, one or more of the ion funnels 32 and/or one or more of the drift tube sub-sections 30 may include one or more ion gates controllable in a conventional manner to selectively pass ions therethrough or block ions from passing therethrough. Alternatively or additionally, one or more of the ion funnels 32 may include one or more regions that is/are controllable in a conventional manner to modify the structures of some or all of the ions passing therethrough, e.g., via ion fragmentation and/or inducing conformational changes in the ions. Further details relating to illustrative embodiments of the drift tube sub-sections 30 and the drift tube funnels 32 shown in FIG. 1A and described above are described in U.S. Patent Pub. No. 2007/0114382 A1 and also in related U.S. Pat. No. 8,618,475, the disclosures of which are incorporated herein by reference.

The transition drift tube section DT in the embodiment illustrated in FIG. 1A, is illustratively made up of a number, S, of curved drift tube sub-sections $34_S$ (two such curved drift tube sub-sections $34_1$ and $34_2$ shown, with the curved drift tube sub-section $34_1$ defining an ion inlet to the transition drift tube section DT and coupled to the ion outlet of the first drift tube section D1, and with the curved drift tube sub-section $34_2$ defining an ion outlet of the transition drift tube section DT and coupled to the ion inlet of the second drift tube section D2), a number, T, of the drift tube funnels $32_T$ (three such drift tube funnels $32_3$, $32_4$ and $32_5$ shown) and sub-sections of each of two curved, Y-shaped drift tube sections $36_1$ and $36_2$. The multiple-pass ion mobility spectrometer 14, in the embodiment illustrated in FIG. 1A, is illustratively provided in the form of a closed-path drift tube made up of a number, U, of the curved drift tube sub-sections $34_U$ (two such curved drift tube sub-sections $34_3$ and $34_4$ shown), remaining sub-sections of the two curved, Y-shaped drift tube sections $36_1$ and $36_2$, and a number, V, of the drift tube funnels $32_V$ (four such drift tube funnels $32_5$, $32_6$, $32_7$ and $32_8$ shown). It will be understood, however, that the multiple-pass drift tube 14 may alternatively not form a closed path but may nevertheless be configured to pass ions multiple times therethrough.

In the embodiment illustrated in FIG. 1A, the sub-section or branch of the curved, Y-shaped drift tube section $36_1$ that is coupled to the drift tube funnel $32_3$ serves the dual function as part of the single-pass ion mobility spectrometer 12 and also as an ion inlet to the multiple-pass ion mobility spectrometer 14, and the sub-section or branch of the curved, Y-shaped drift tube section $36_2$ that is coupled to the drift tube funnel $32_4$ likewise serves the dual function as part of the single-pass ion mobility spectrometer 12 and also as an ion outlet of the multiple-pass ion mobility spectrometer 14. The drift tube funnel $32_5$ is illustratively shared by the single-pass ion mobility spectrometer 12 and the multiple-pass ion mobility spectrometer 14 and therefore forms part of each. Further details relating to illustrative embodiments of the curved drift tube sub-sections 34, the curved Y-shaped drift tube sections 36 and the closed-path configuration of the multiple-pass ion mobility spectrometer 14 shown in FIG. 1A and described above are described in U.S. Pat. No. 8,362,420, the disclosure of which is incorporated herein by reference.

The hybrid ion mobility spectrometer 10 illustrated in FIG. 1A includes three ion gates, G1-G3, each of which is controllable in a conventional manner to selectively allow ions to pass therethrough and to selectively block ions from passing therethrough. In one embodiment, the ion gates G1-G3 are each provided in the form of a mesh or grid, and a DC potential applied thereto, or a DC differential applied between a mesh or grid and an adjacent ring, is controlled such that at one DC level or DC differential value ions pass through the ion gate and at a different DC level or DC differential value ions are blocked from passing through the ion gate. In alternate embodiments, the ion gate function of one or more of the ion gates G1-G3 may be accomplished by selectively applying and varying the frequency and/or amplitude of an RF voltage to a non-meshed or gridded ring, in a conventional manner, to selectively allow passage or block passage of ions therethrough. In some embodiments, one or more of the gates G1-G3 may be controlled with intermediate DC potentials and/or RF frequencies/amplitudes to pass therethrough only a portion of ions presented thereat, e.g., to allow passage through one or more of the ion gates G1-G3 of only a percentage of ions that is less than 100% of the total number of ions traveling toward the one or more ion gates G1-G3. In any case, the three ion gates G1-G3 are controllable, as will be described in detail below, to confine ions within the single-pass drift tube 12, to confine ions within the multiple-pass drift tube 14, to pass or divert at least some of the ions in the single-pass drift tube 12 into the multiple-pass drift tube 14 and/or to pass or divert at least some of the ions in the multiple-pass drift tube 14 back into the single-pass drift tube 12.

In the embodiment illustrated in FIG. 1A, a first one of the ion gates, G1, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_8$. A second one of the ion gates, G2, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_4$. A third one of the ion gate, G3, is illustratively positioned in the curved, Y-shaped drift tube section $36_1$ at an interface of the sub-section of the Y-shaped drift tube section $36_1$ that is coupled to the drift tube funnel $32_5$ and the sub-section or branch of the Y-shaped drift tube section $36_1$ that is coupled to the drift tube funnel $32_3$. It will be understood that the hybrid ion mobility spectrometer 10 may include more or fewer such ion gates, and that any such alternative embodiment of the hybrid ion mobility spectrometer is contemplated by this disclosure.

In one alternate embodiment of the hybrid ion mobility spectrometer 10, one or more of the drift tube sub-sections 30, 34, 36 and/or one or more of the drift tube funnels 32 may be provided in the form of a two-part sub-section or funnel defining a first drift tube region having an ion inlet defining the ion inlet of the sub-section or funnel and an ion outlet coupled to an ion inlet of an ion elimination region having an ion outlet defining the ion outlet of the sub-section or funnel. Further details relating to the structure and various operational modes of such alternately configured drift tube sub-sections and/or funnels are described in co-pending U.S. Patent Application Pub. No. 2013/0292562, the disclosure of which is incorporated herein by reference.

Figure 2:
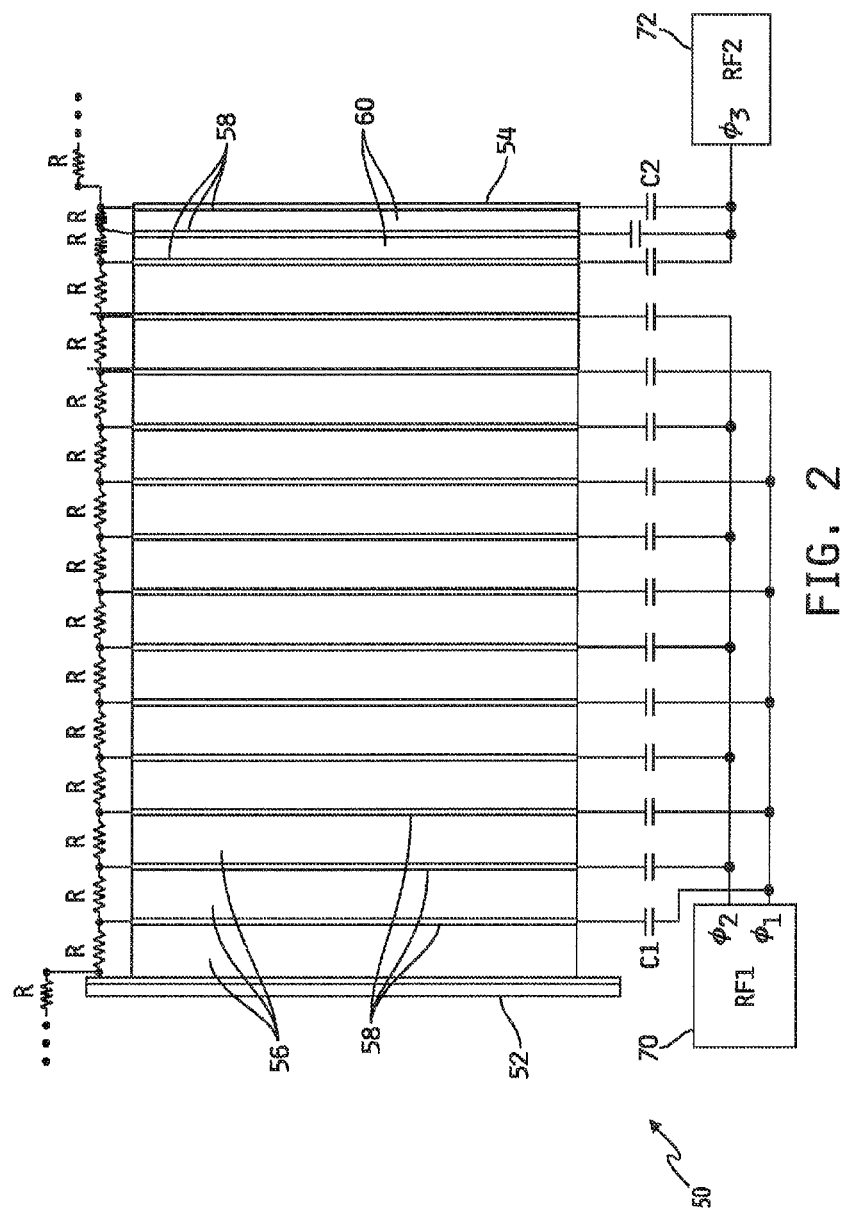
FIG. 2 is a simplified diagram of an embodiment of a drift tube segment that may be used in any of the hybrid ion mobility spectrometers of FIGS. 1A-1C.

In another alternate embodiment of the hybrid ion mobility spectrometer 10, one or more of the drift tube funnels 32 and/or one or more of the drift tube sub-sections 30, 34, 36 may be provided in the form of a conventional drift tube sub-section 30 to which RF voltages may be applied to radially focus ions inwardly toward the ion drift path defined therethrough. One illustrative embodiment of such a drift tube sub-section 50 is shown in FIG. 2, and includes a series of identically-dimensioned, electrically insulating rings 56 each separating adjacent ones of a series of identically-dimensioned, electrically conductive rings 58, with all such rings 56, 58 stacked and clamped together between an ion inlet 52 and an ion outlet 54 of the drift tube sub-section 50. Illustratively, the last several, e.g., two, electrically insulating rings may be (but need not be) provided in the form of reduced-thickness rings 60 (e.g., approximately ½ of the thickness of the rings 56), the purpose which will be described below.

In the illustrated embodiment, an RF voltage source 70 produces two RF voltages, $\Phi_1$ and $\Phi_2$ each 180 degrees out of phase with respect to the other, with $\Phi_1$ applied via a separate capacitor, C1, to all odd (or even) numbered rings 58 and $\Phi_2$ applied via a separate capacitor, C1, to all even (or odd) numbered rings 58 such that $\Phi_1$ and $\Phi_2$ are applied alternately to the series of rings 58 in the stack. A DC potential is applied via series-connected resistors, R, to the rings 58 to create a substantially uniform electric drift field in the drift tube sub-section 50, and ions drift through the drift tube sub-section 50 under the influence of the electric drift field. The frequencies and/or amplitudes of the RF voltages $\Phi_1$ and $\Phi_2$ are illustratively selected in a conventional manner to radially focus ions drifting through the drift tube sub-section 50 toward an ion drift axis defined centrally through the drift tube sub-section 50. In embodiments in which the reduced-width, electrically insulating rings 60 are included, another RF voltage source 72 may be provided to produce an RF voltage $\Phi_3$ that is applied through a different capacitor, C2, to each of the electrically conductive rings 58 contacting one of the rings 60. The frequency and/or amplitude of $\Phi_3$ is controlled in a conventional manner to selectively allow passage of ions through the electrically conductive rings 58 connected to $\Phi_3$ or block passage of ions therethrough to thereby provide an ion gating function.

The drift tube sub-sections 50 with the radial ion focusing feature described above may be used in place of one or more of the drift tube funnels 32 and/or in place of one or more of the drift tube sub-sections 30, 34, 36 illustrated in FIG. 1A. Alternatively or additionally, the drift tube sub-sections 50 with or without the radial ion focusing feature but with the ion gating feature described above may be used in place of one or more of the ion gates G1-G3 illustrated in FIG. 1A. In any of the embodiments illustrated in the attached figures and described herein, either or both of the single-pass drift tube and the multiple-pass drift tube may be operated in a conventional traveling wave operating mode, i.e., one in which one or more oscillating, i.e., AC, electric fields are established within the various drift tube sections to cause the ions to separate as they drift through the respective drift tube.

Referring again to FIG. 1A, a number of voltage sources 40 are electrically connected to various parts of the hybrid ion mobility spectrometer 10, and the number of voltage sources 40 are selected and controlled to apply appropriate DC and/or AC voltages to the various parts and components of the hybrid ion mobility spectrometer 10 for operation thereof. For example, one or more of the voltage sources 40 is/are electrically connected to the ion source 18 to control the ion source 18 in a conventional manner to generate, collect and/or process ions as described above. One or more others of the voltage sources 40 is/are electrically connected to each drift tube sub-section 30, 34, 36 and each drift tube funnel 32 to establish an electric drift field therein through which ions traverse the single-pass drift tube 12 and the multiple-pass drift tube 14. One or more others of the voltage sources 40 is/are electrically connected to the drift tube funnels 32 to radially focus ions inwardly toward the drift tube axis defined therethrough, and/or to control operation of one or more ion gates contained therein to pass or block ions, and/or to control one or more ion activation regions included in one or more of the funnels 32 to modify the structure of ions passing therethrough, e.g., via ion fragmentation and/or by inducing conformational changes in ions without fragmenting them. One or more others of the voltage sources 40 is/are electrically connected to each of the ion gates G1-G3 and selectively controlled to pass or block ions as described above and as will be described in greater detail below with respect to the process illustrated in FIG. 3. In any case, the one or more voltage sources 40 are conventional and may be individually programmed for operation or controlled by a processor 42 (e.g., amplitude, frequency, timing of activation and/or deactivation, etc.) as shown by dashed-line representation. The processor 42 is, in any event, electrically connected to the ion detector, and the processor 42 includes a memory having instructions stored therein that are executable by the processor 42 to process ion detection signals produced by the ion detector 22 and produce corresponding ion mobility spectral information, e.g., as a function of ion drift time through the single-pass drift tube 12 and/or the multiple-pass drift tube 14.

A gas source 44, e.g., single buffer gas, combination of gases to form a buffer gas, one or a combination of other gases, etc., is fluidly coupled to the hybrid ion mobility spectrometer 10 via a fluid conduit 46. In embodiments of the hybrid ion mobility spectrometer 10 constructed from open-ended sub-sections 30, 34, 36 and with or without open-ended drift tube funnels 32, the resulting spectrometer 10 is a continuous cavity spectrometer, and the single gas source 44 may thus be used to fill the entire spectrometer 10, including the single-pass drift tube 12 and the multiple-pass drift tube 14. In alternative embodiments, two or more gas sources may be used, and the hybrid ion mobility spectrometer 10 may be partitioned in a conventional manner to confine the two or more gases to corresponding portions of the spectrometer 10. The gas source 44 may be manually controlled, programmable for automatic control and/or controlled by the processor 42 as shown by dashed-line representation in FIG. 1A.

Referring now to FIG. 1B, an alternate embodiment of a hybrid ion mobility spectrometer 10' is shown. The hybrid ion mobility spectrometer 10' is identical in many respects to the hybrid ion mobility spectrometer 10 illustrated in FIG. 1A and described above. Like features are identified by like reference numbers, and a detailed description of common features between the two spectrometers 10 and 10' will not be repeated here for brevity. It will be further understood that the various embodiments of the various components and aspects to the hybrid ion mobility spectrometer 10 described above apply equally to the hybrid ion mobility spectrometer 10'.

The hybrid ion mobility spectrometer 10' illustrated in FIG. 1B differs from the hybrid ion mobility spectrometer 10 illustrated in FIG. 1A primarily in the construction of the single-pass drift tube 12' and in the number and location of the various ion gates that are controlled to achieve operation of the spectrometer 10 as described above. In the embodiment illustrated in FIG. 1B, for example, the drift tube funnel $32_3$ is coupled at its ion inlet to one ion outlet branch of a Y-shaped drift tube sub-section $38_1$ having another ion outlet branch coupled to an ion inlet of another drift tube funnel $32_{11}$, wherein both such ion outlet branches are coupled to a common ion inlet branch having an ion inlet coupled to an ion outlet of the drift tube funnel $32_2$. The drift tube funnel $32_4$ is similarly coupled at its ion outlet to one ion inlet branch of another Y-shaped drift tube sub-section $38_2$ having another ion inlet branch coupled to an ion outlet of the drift tube funnel $32_{11}$, wherein both such ion outlet branches are coupled to a common ion outlet branch having an ion outlet coupled to an ion outlet of the drift tube funnel $32_9$. In this embodiment, the single-pass drift tube 12' is a linear drift tube made up of the linear drift tube segments D1 and D2 joined by a linear drift tube segment D3 made up of the linear branches of the Y-shaped drift tube sub-sections $38_1$, $38_2$ and the drift tube funnel $32_{11}$.

The embodiment illustrated in FIG. 1B includes four ion gates G1-G4 which are controllable, as will be described in detail below, to confine ions within the single-pass drift tube 12', to confine ions within the multiple-pass drift tube 14, to pass or divert at least some of the ions in the single-pass drift tube 12' into the multiple-pass drift tube 14 and/or to pass or divert at least some of the ions in the multiple-pass drift tube 14 back into the single-pass drift tube 12'. A first one of the ion gates, G1, is illustratively positioned in the Y-shaped drift tube section $38_1$ at an interface of the curved branch of the Y-shaped drift tube section $38_1$ that is coupled to the drift tube funnel $32_1$ and the branch of the Y-shaped drift tube section $38_1$ that is coupled to the drift tube funnel $32_2$. A second one of the ion gates, G2, is illustratively positioned in the Y-shaped drift tube section $38_1$ at an interface of the linear branch of the Y-shaped drift tube section $38_1$ that is coupled to the drift tube funnel $32_{11}$ and the branch of the Y-shaped drift tube section $38_1$ that is coupled to the drift tube funnel $32_2$. A third one of the ion gates, G3, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_8$. A fourth one of the ion gates, G4, is illustratively positioned in the curved, Y-shaped drift tube section $36_2$ at an interface of the sub-section of the Y-shaped drift tube section $36_2$ that is coupled to the drift tube funnel $32_5$ and the sub-section or branch of the Y-shaped drift tube section $36_2$ that is coupled to the drift tube funnel $32_4$. It will be understood that the hybrid ion mobility spectrometer 10' may include more or fewer such ion gates, and that any such alternative embodiment of the hybrid ion mobility spectrometer is contemplated by this disclosure.

Figure 1C:
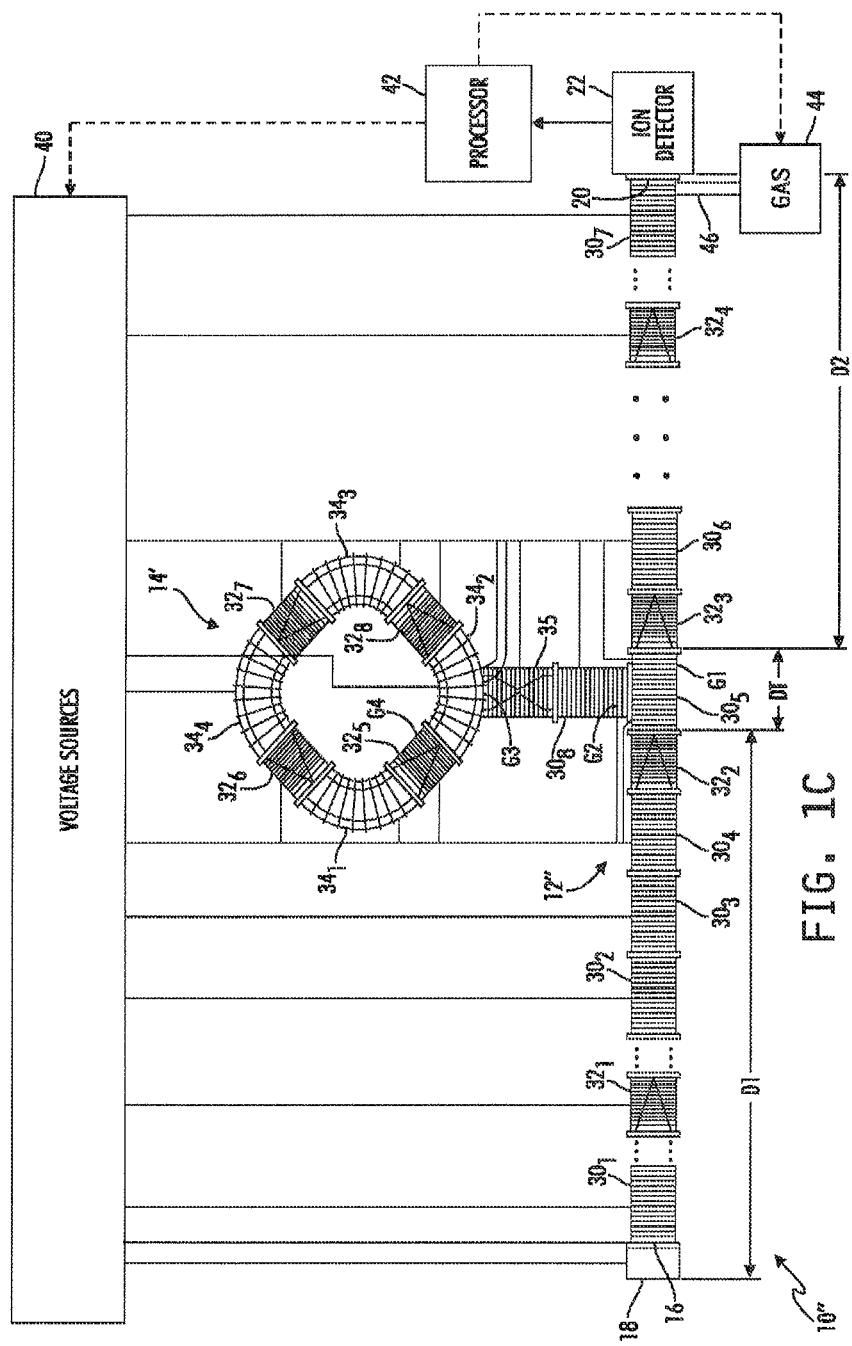
FIG. 1C is a simplified diagram of another alternate embodiment of a hybrid ion mobility spectrometer.

Referring now to FIG. 1C, another alternate embodiment of a hybrid ion mobility spectrometer 10" is shown. The hybrid ion mobility spectrometer 10" is also identical in many respects to the hybrid ion mobility spectrometer 10 illustrated in FIG. 1A and described above. Like features are identified by like reference numbers, and a detailed description of common features between the two spectrometers 10 and 10" will not be repeated here for brevity. It will be further understood that the various embodiments of the various components and aspects to the hybrid ion mobility spectrometer 10 described above apply equally to the hybrid ion mobility spectrometer 10".

The hybrid ion mobility spectrometer 10" illustrated in FIG. 1C differs from the hybrid ion mobility spectrometer 10 illustrated in FIG. 1A primarily in the construction of each of the single-pass drift tube 12" and the multiple-pass drift tube 14', and also in the location of the various ion gates that are controlled to achieve operation of the spectrometer 10 as described above. In the embodiment illustrated in FIG. 1C, for example, the drift tube funnel $32_2$ is coupled at its ion outlet to an ion inlet of a drift tube sub-section $30_5$, and an ion outlet of the drift tube sub-section $30_5$ is coupled to an ion inlet of the drift tube funnel $32_3$ (corresponding to the drift tube funnel $32_9$ in FIG. 1A). In this embodiment, the single-pass drift tube 12" is thus a linear drift tube made up of the linear drift tube segments D1 and D2 joined by a linear drift tube segment DT made up of the drift tube sub-section $30_5$. The multiple-pass drift tube 14' is, in the embodiment illustrated in FIG. 1C, a closed-path drift tube made up of four curved drift tube sub-sections $34_1$-$34_4$ each coupled between a different two of four drift tube funnels $32_5$-$32_8$. A drift tube section $30_8$ has an ion inlet coupled to the drift tube sub-section $30_5$ of the single-pass drift tube 12" and an ion outlet coupled to an ion inlet of a drift tube section 35. An ion outlet of the drift tube section 35 is coupled to the drift tube sub-section $34_2$ of the multiple pass drift tube 14'. In some embodiments, such as that illustrated in FIG. 1C, the drift tube section 35 may include an inlet/outlet, i.e. bi-directional, funnel which may be controlled in a conventional manner, e.g., via one or more voltage sources, to direct and focus ions moving from the single-pass drift tube 12" into the multiple-pass drift tube 14' via the drift tube sub-section $30_8$, and which may also be controlled in a conventional manner, e.g., via one or more voltage sources, to direct and focus ions moving from the multiple-drift tube 14' into the single-pass drift tube 12" via the drift tube sub-section $30_8$. In other embodiments, the bi-directional funnel may be replaced with another funnel structure or other mechanism (e.g., structure and/or energy source(s)), or omitted altogether. In any case, the drift tube sections $30_8$, 35 form a T-connection between the single pass drift tube 12" and the multiple-pass drift tube 14'.

The embodiment illustrated in FIG. 1C includes three ion gates G1-G3 which are controllable, as will be described in detail below, to confine ions within the single-pass drift tube 12", to confine ions within the multiple-pass drift tube 14', to pass or divert at least some of the ions in the single-pass drift tube 12" into the multiple-pass drift tube 14' and/or to pass or divert at least some of the ions in the multiple-pass drift tube 14' back into the single-pass drift tube 12". A first one of the ion gates, G1, is illustratively positioned in the drift tube sub-section $30_5$ at or just beyond the ion inlet of the drift tube section $30_8$. A second one of the ion gates, G2, is illustratively positioned in the drift tube section $30_8$ at or just beyond the ion inlet thereof. A third one of the ion gates, G3, is illustratively positioned in the drift tube section 35 at or near the ion outlet thereof. It will be understood that the hybrid ion mobility spectrometer 10" may include more or fewer such ion gates, and that any such alternative embodiment of the hybrid ion mobility spectrometer is contemplated by this disclosure.

Figure 1D:
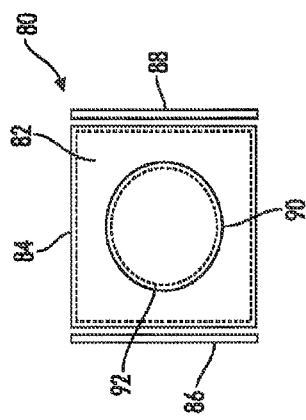
FIG. 1D is a simplified diagram of yet another alternate embodiment of a hybrid ion mobility spectrometer.
Figure 1F:
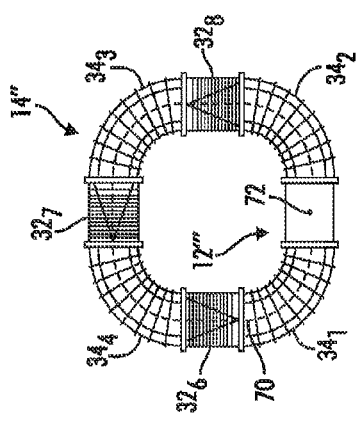
FIG. 1F is a simplified diagram of an embodiment of the transition region of the hybrid ion mobility spectrometer illustrated in FIGS. 1D and 1E.
Figure 1E:
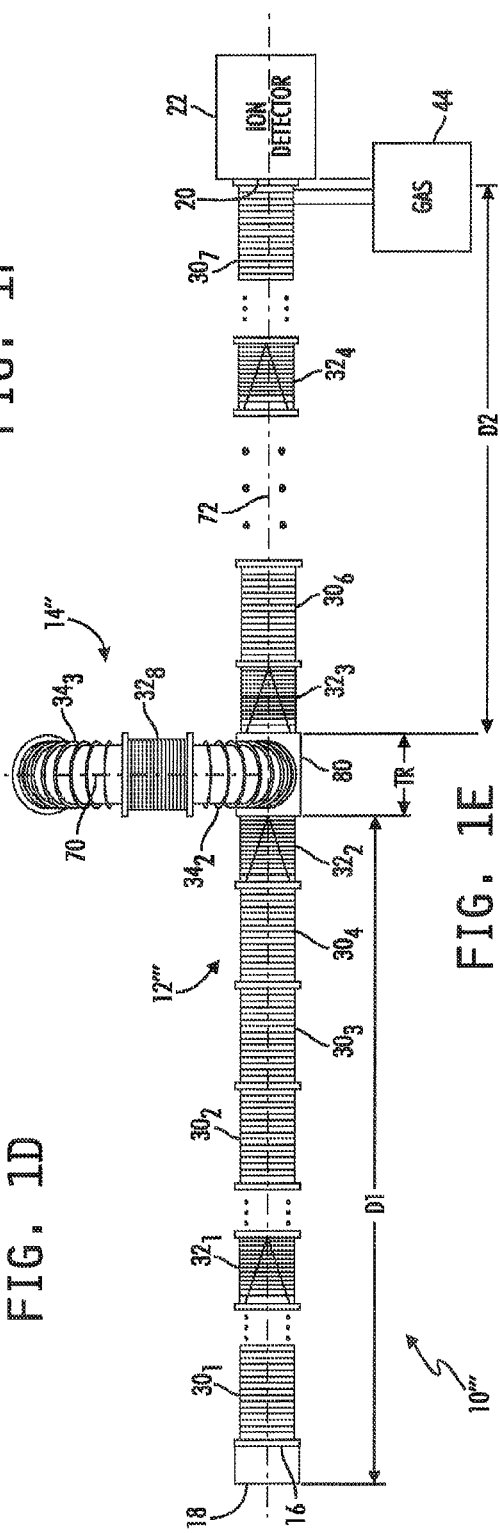
FIG. 1E is a simplified diagram of the embodiment illustrated in FIG. 1D viewed orthogonally from the view illustrated in FIG. 1D.

Referring now to FIGS. 1D-1F, yet another alternate embodiment of a hybrid ion mobility spectrometer 10''' is shown. The hybrid ion mobility spectrometer 10''' is also identical in many respects to the hybrid ion mobility spectrometers 10 and 10" illustrated in FIGS. 1A and 1C respectively and described above. Like features are identified by like reference numbers, and a detailed description of common features between the spectrometers 10, 10" and 10''' will not be repeated here for brevity. It will be further understood that the various embodiments of the various components and aspects to the hybrid ion mobility spectrometer 10 and 10″ described above apply equally to the hybrid ion mobility spectrometer 10‴.

In one aspect, the hybrid ion mobility spectrometer 10‴ illustrated in FIGS. 1D-1F differs from the hybrid ion mobility spectrometer 10 and 10″ illustrated in FIGS. 1A and 1C respectively in that an ion travel axis 70 of the multiple-pass drift tube 14″, i.e., an axis defined, or parallel with an axis defined, centrally through the multiple-pass drift tube 14″ and along which ions travel through the multiple-pass drift tube 14″, lies in a plane that is different from the plane in which an ion travel axis 72 of the single-pass drift tube 12‴, i.e., an axis defined, or parallel with an axis defined, centrally through the single-pass drift tube 12‴ and along which ions travel through the single-pass drift tube 12‴, lies. In the illustrated embodiment, the planes in which the ion travel axes 70 and 72 lie are orthogonal, although it will be understood that this disclosure contemplates embodiments in which the two different planes in which the ion travel axes 70 and 72 lie are not orthogonal.

In another aspect, the hybrid ion mobility spectrometer 10‴ illustrated in FIGS. 1D-1F differs from the hybrid ion mobility spectrometer 10 and 10″ illustrated in FIGS. 1A and 1C respectively in that, in contrast to a drift tube transition section, DT, the hybrid ion mobility spectrometer 10‴ defines a transition region 80 (TR) as an interface between the single-pass drift tube 12‴ and the multiple-pass drift tube 14″. Referring specifically to FIG. 1F, an example embodiment of the transition region 80 is illustrated. In this embodiment, the transition region 80 includes a first plate 82 defining an ion passage, e.g., opening, 90 therethrough, which represents an ion inlet to the transition region 80 positioned adjacent to the ion outlet of the drift tube funnel 32₂ (e.g., see FIG. 1E). Another plate 84 is positioned opposite to the plate 80 and defines another ion passage, e.g., opening, 92 therethrough (both shown by dashed-line representation in FIG. 1F), which represents an ion outlet of the transition region 80 positioned adjacent to the ion inlet of the drift tube funnel 32₃. A third plate 86 is positioned between the plates 82 and 84 along one side thereof, and a fourth plate 88 is positioned between the plates 82 and 84 along another side thereof. The third and fourth plates 86, 88 each define an ion passage, e.g., opening, therethrough which represent an ion inlet/outlet to/of the transition region 80 with the opening defined through the plate 86 positioned adjacent to the ion inlet/outlet of the drift tube sub-section 34₁ and the opening defined through the plate 88 positioned adjacent to the ion inlet/outlet of the drift tube section 34₂. One or more of the plates 82, 84, 86, 88 may illustratively be operated as an ion gate, such that the illustrated embodiment may include one or more of G1-G4.

Figure 3A:
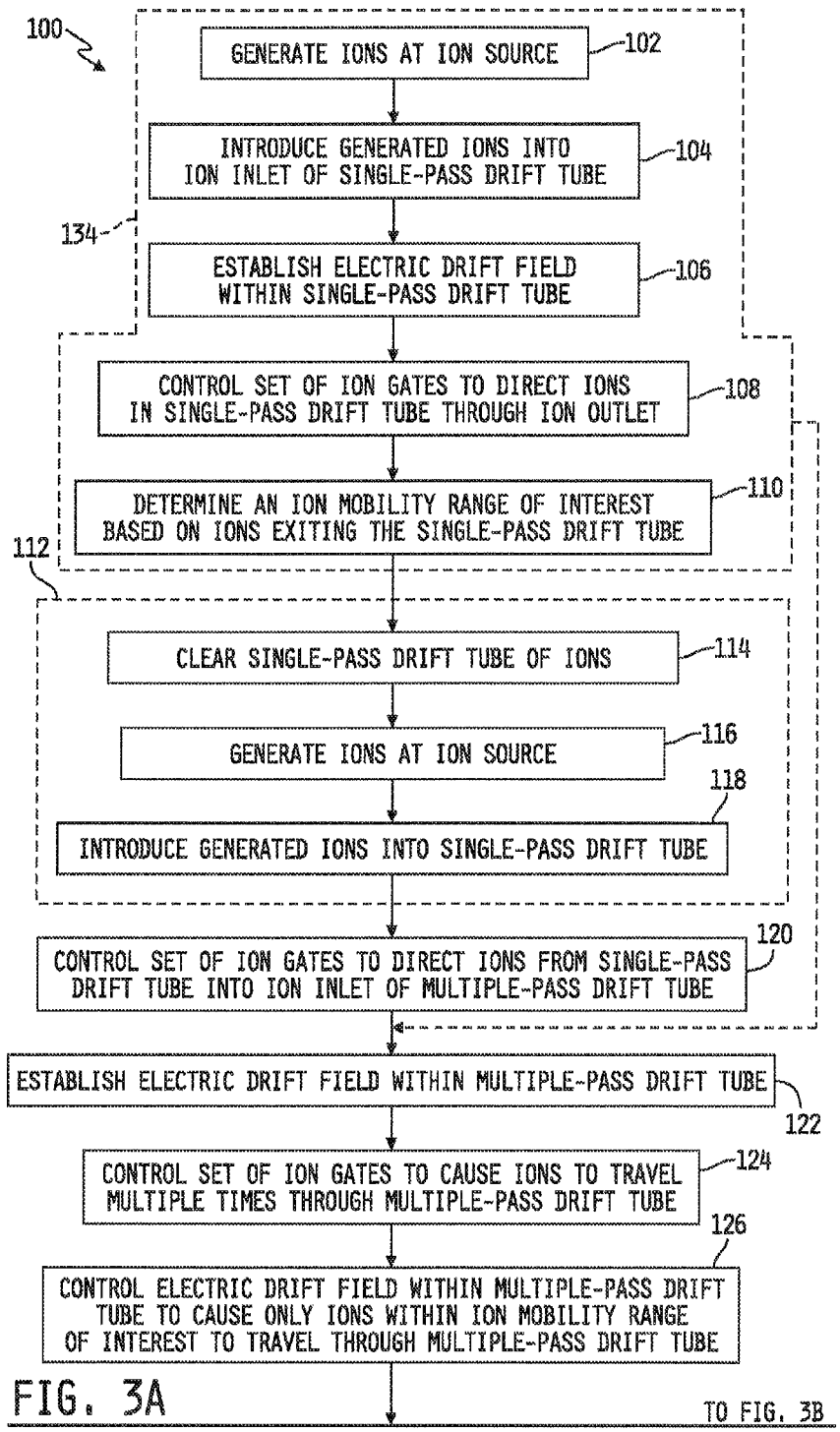
FIG. 3 includes FIGS. 3A and 3B and is a simplified flowchart of an embodiment of a process for separating ions using any of the hybrid ion mobility spectrometers of FIGS. 1A-1F.
Figure 3B:
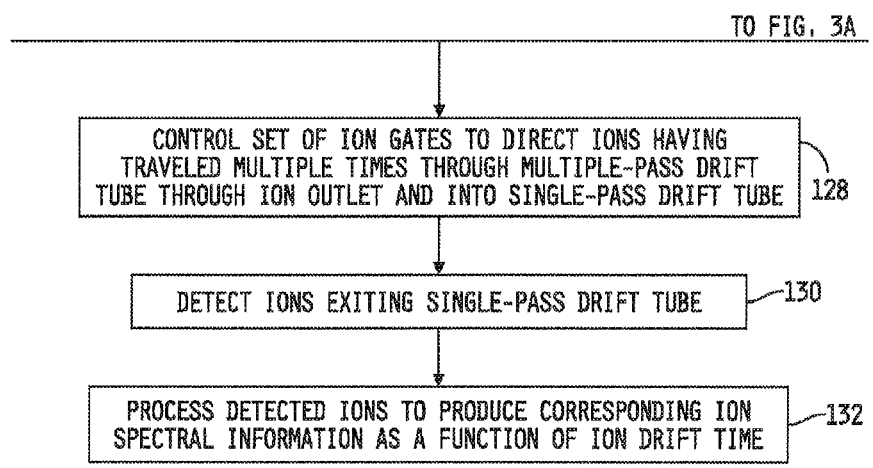

As described briefly hereinabove, the ion gates G1-G3 of the hybrid ion mobility spectrometers 10 and 10″ and the ion gates G1-G4 of the hybrid ion mobility spectrometer 10′ and 10‴ are controllable to confine ions within the single-pass drift tube 12, 12′, 12″, 12‴, to confine ions within the multiple-pass drift tube 14, 14′, 14″ to pass or divert at least some of the ions in the single-pass drift tube 12, 12′, 12″, 12‴ into the multiple-pass drift tube 14, 14′, 14″ and/or to pass or divert at least some of the ions in the multiple-pass drift tube 14, 14′, 14″ back into the single-pass drift tube 12, 12′, 12″, 12‴. Referring now to FIGS. 3A and 3B, a flowchart is shown illustrating a process 100 for controlling the hybrid ion mobility spectrometer 10, 10′, 10″, 10‴ according to a number of different operational modes of the hybrid ion mobility spectrometer 10, 10′, 10″, 10‴ in which the set of ion gates, e.g., ion gates G1-G3 for the spectrometers 10, 10″ and ion gates G1-G4 for the spectrometer 10′, 10‴, are controlled as described above. In one embodiment, some or all of the process 100 may be controlled by the processor 42 in accordance with instructions stored in a memory of the processor 42. Alternatively or additionally, some or all of the process 100 may be controlled by programming one or more of the one or more voltage sources 40 in embodiments in which one or more of the voltage sources 40 are programmable. Some of the process 100 may be alternatively or additionally carried out manually.

In any case, the process 100 begins at step 102 where the ion source 18 is controlled in a conventional manner to generate ions, e.g., in embodiments in which the ion source 18 is or includes an ion generation structure for generating ions from a sample, or to otherwise supply ions, e.g., in embodiments in which the ion source 18 is another ion separation instrument and/or other ion processing instrument that does not itself generate ions but rather operates on ions generated elsewhere. Thereafter at step 104, at least some of the generated or otherwise supplied ions are introduced into the ion inlet 16 of the single-pass drift tube 12, 12′, 12″, 12‴, e.g., by controlling a conventional ion gate positioned at the ion inlet 16 to pass ions therethrough and into the single-pass drift tube 12, 12′, 12″, 12‴, by drawing generated ions into the single-pass drift tube 12, 12′, 12″, 12‴ using a static or dynamic electric field, or the like. At step 106, an electric drift field is established within the single-pass drift tube 12, 12′, 12″, 12‴, which may occur before or after step 104.

In any case, the process 100 advances to step 108 where the ion gates, e.g., G1-G3 in the case of the hybrid ion mobility spectrometer 10, 10″ and G1-G4 in the case of the hybrid ion mobility spectrometer 10′, 10‴, are controlled to direct ions in the single-pass drift tube 12, 12′, 12″, 12‴ therethrough and through the ion outlet 20, i.e., to confine ions within the single-pass drift tube 12, 12′, 12″, 12‴ such that the ions drift only through the single-pass drift tube 12, 12′, 12″, 12‴ from the ion inlet 16 to the ion outlet 20 thereof and not through the multiple-pass drift tube 14, 14′, 14″. In the single-pass drift tube 12 illustrated in FIG. 1A, step 108 may be carried out by controlling G1 to the closed or ion-blocking position and controlling G2 and G3 to the open or ion-passing position, such that ions entering the ion inlet 16 pass sequentially through D1, DT and D2 of the single-pass drift tube 12. In the single-pass drift tube 12′ illustrated in FIG. 1B, step 108 may be carried out by controlling G1 to the closed or ion-blocking position and controlling G2 to the open or ion-passing position, such that ions entering the ion inlet 16 pass sequentially through D1, D3 and D2 of the single-pass drift tube 12′. In the single-pass drift tube 12″ illustrated in FIG. 1C, step 108 may be carried out by controlling G1 to the open or ion-passing position and controlling G2 to the closed or ion-blocking position, such that ions entering the ion inlet 16 pass sequentially through D1, DT and D2 of the single-pass drift tube 12″. In the single-pass drift tube 12‴ illustrated in FIGS. 1D-1F, step 108 may be carried out by controlling G1, e.g., the opening 90 through the plate 82, to the open or ion-passing position and controlling G2, e.g., the opening 92 through the plate 84, to the open or ion-passing position, and likewise controlling the gates G3, G4, .e.g., the openings through the plates 86, 88 respectively to the closed or ion blocking positions, such that ions entering the ion inlet 16 pass sequentially through D1, TR and D2 of the single-pass drift tube 12‴. In each case, ions generated at or otherwise supplied by the ion source 18 travel, i.e., drift, through only the single-pass drift tube 12, 12', 12", 12''' under the influence of the electric field established therein where they separate in time as a first function of ion mobility defined by the various structural dimensions and operating parameters of the single-pass drift tube 12, 12', 12", 12'''.

Following step 108, the process 100 advances to step 110 where an ion mobility range of interest is determined based on at least some of the ions exiting the single-pass drift tube 12, 12', 12", 12'''. As described above, it may be discovered upon analysis of ion spectral information resulting from the detection of ions exiting the ion outlet 20 of the single-pass drift tube 12, 12', 12', 12''' pursuant to step 108 that a subset, e.g., two or more, of ion intensity peaks in a particular range of ion mobilities (or ion drift times) are crowded together and cannot be satisfactorily resolved over the length of the single-pass drift tube 12, 12', 12", 12'''. Such a range of ion mobilities may then be the ion mobility range of interest. In other cases, the ion mobility range of interest may be determined based on one or more alternate or additional criteria. In some cases, the ion mobility range of interest may be the same as that produced by the single-pass drift tube 12, 12', 12", 12''', and in other cases the ion mobility range of interest may be different as just described. Likewise, whereas the single-pass drift tube 12, 12', 12", 12''' is generally operable to separate ions according to a first function of ion mobility and the multiple-pass drift tube 14, 14', 14" is generally operable to separate ions according to a second function of ion mobility, the first and second functions of ion mobility may be the same in some embodiments and different in others.

In one embodiment, the process 100 includes a step 112 as shown in dashed-line representation, and in this embodiment the process 100 advances from step 110 to step 114 wherein the single-pass drift tube 12, 12', 12", 12''' is cleared of ions, e.g., by stopping the generation of ions by the ion source 18 and allowing the tube 12, 12', 12", 12''' to clear. Thereafter at step 116, the ion source 18 is controlled to begin generating ions again, and thereafter at step 118 at least some of the generated ions are introduced into the single-pass drift tube 12, 12', 12", 12''' as described above with respect to step 104. In alternate embodiments, the process 100 does not include step 112 and in some such embodiments the ion source 18 may be controlled to continually, periodically or intermittently generate ions while in other embodiments the ion source 18 may be started and then stopped, but ions need not be cleared from the single-pass drift tube 12, 12', 12", 12''' before continuing to step 120.

At step 120, the set of ion gates, e.g., G1-G3 in the case of the hybrid ion mobility spectrometer 10, 10" and G1-G4 in the case of the hybrid ion mobility spectrometer 10', 10''', is controlled to divert or pass some or all of the ions in or entering the single-pass drift tube 12, 12', 12", 12''' into the multiple-pass drift tube 14, 14', 14", and at step 122 an electric field is established within the multiple-pass drift tube 14, 14', 14" to cause ions to drift through the multiple-pass drift tube 14, 14', 14". In the single-pass drift tube 12 illustrated in FIG. 1A, step 120 may be carried out by controlling G1 and G3 to their open or ion-passing positions and controlling G2 to the closed or ion-blocking position, such that ions entering the ion inlet 16 pass sequentially through D1, through part of DT and into the multiple-pass drift tube 14. In the single-pass drift tube 12' illustrated in FIG. 1B, step 120 may be carried out by controlling G1 and G3 to their open or ion-passing positions, and controlling G2 and G4 to their closed or ion-blocking positions, such that ions entering the ion inlet 16 pass from D1 directly into the multiple-pass drift tube 14. In the single-pass drift tube 12" illustrated in FIG. 1C, step 120 may be carried out by controlling G1 to the closed or ion-blocking position, and controlling G2 and G3 to their open or ion-passing positions with the electric drift field in the drift tube sections $30_8$ and 35 controlled to pass ions moving through D1 into the multiple-pass drift tube 14'. In the single-pass drift tube 12''' illustrated in FIGS. 1D-1F, step 120 may be carried out by controlling G1, e.g., the opening 90 through the plate 82, to the open or ion-passing position, controlling G2, e.g., the opening 92 through the plate 84, to the closed or ion-blocking position, and controlling the gates G3 and/or G4, .e.g., the openings through the plates 86, 88 respectively to the open or ion-passing positions, such that ions entering the ion inlet 16 pass from D1 through TR and directly into the multiple-pass drift tube 14". Ions generated at the ion source 18 thus travel, i.e., drift, through the single-pass drift tube 12, 12', 12", 12''' under the influence of the electric field established therein where they separate in time as a first function of ion mobility defined by the various structural dimensions and operating parameters of the single-pass drift tube 12, 12', 12", 12''', and after passage of some or all of such ions into the multiple-pass drift tube 14, 14', 14" the ions travel, i.e., drift, through the multiple-pass drift tube 14, 14', 14" under the influence of the electric field established therein where they separate in time as a second function of ion mobility defined by the various structural dimensions and operating parameters of the multiple-pass drift tube 14, 14', 14". The first and second functions of ion mobility may be the same in some embodiments and different in others.

At step 124, the set of ion gates, e.g., G1-G3 in the case of the hybrid ion mobility spectrometer 10, 10" and G1-G4 in the case of the hybrid ion mobility spectrometer 10', 10''', is controlled to cause ions within the multiple-pass drift tube 14, 14, 14" to travel one or multiple times through or about the multiple-pass drift tube 14, 14', 14". The number of times the ions travel through or about the multiple-pass drift tube 14, 14', 14" will typically be dictated by the total length of the multiple-pass drift tube 14, 14', 14" needed to adequately resolve the ion peaks of interest, or by other additional or alternate criteria. In the single-pass drift tube 12 illustrated in FIG. 1A, step 124 may be carried out by maintaining G1 in its open or ion-passing position and G2 in its closed or ion-blocking position, and controlling G3 to its closed position such that the multiple-pass drift tube 14 is completely closed to the single-pass drift tube 12. In the single-pass drift tube 12' illustrated in FIG. 1B, step 124 may be carried out by maintaining G3 and in its open or ion-passing position and G4 in its closed or ion-blocking position, and controlling G1 to its closed or ion-blocking position such that the multiple-pass drift tube 14 is completely closed to the single-pass drift tube 12'. In the single-pass drift tube 12" illustrated in FIG. 1C, step 124 may be carried out by controlling G2 and/or G3 to closed or ion-blocking position, such that the multiple-pass drift tube 14' is completely closed to the single-pass drift tube 12". In the single-pass drift tube 12''' illustrated in FIGS. 1D-1F, step 124 may be carried out by controlling G1, G2, e.g., the openings through the plates 82, 84 respectively, to their closed or ion-blocking positions, and controlling G3, G4, .e.g., the openings through the plates 86, 88 respectively, to their open or ion-passing positions, such that the multiple-pass drift tube 14" is completely closed to the single-pass drift tube 12'''. The ions then travel, i.e., drift, through the multiple-pass drift tube 14, 14', 14" under the influence of the electric field established therein where they separate in time as a second function of ion mobility defined by the various structural dimensions and operating parameters of the multiple-pass drift tube 14, 14', 14".

In one embodiment, step 126 is included, and at step 126 the electric drift field established within the multiple-pass drift tube 14, 14', 14" is controlled to cause only ions within the ion mobility range of interest to travel through the multiple-pass drift tube 14, 14', 14". For example, the open/closed timing of the various ion gates (G1-G3 or G1-G4) may be controlled at step 120 to pass ions of all mobilities from the single-pass drift tube 12, 12', 12", 12''' into the multiple-pass drift tube 14, 14', 14", and in such embodiments, electric fields within the sub-sections 34 and funnels 32 of the multiple-pass drift tube 14, 14', 14" are sequentially switched on and off in a conventional manner at a rate that allows only ions within the ion mobility range of interest to traverse the multiple-pass drift tube 14, 14', 14". In some alternate embodiments, the open/closed timing of the ion gates G1-G3 (or G1-G4) may be controlled at step 120 such that only ions within the ion mobility range of interest are passed from the single-pass drift tube 12, 12', 12", 12''' into the multiple-pass drift tube 14, 14', 14", and in such embodiments step 126 may be carried out simply by controlling the application of the electric fields within the sub-sections 34 and funnels 32 of the multiple-pass drift tube 14, 14', 14" to pass ions of all ion mobilities or by sequentially switching such electric fields on and off at a rate that allows only ions within the ion mobility range of interest to continue to traverse the multiple-pass drift tube 14, 14', 14".

After the ions have traveled the multiple times through the multiple-pass drift tube 14, 14', 14" the set of ion gates, e.g., G1-G3 in the case of the hybrid ion mobility spectrometer 10, 10" and G1-G4 in the case of the hybrid ion mobility spectrometer 10', 10''' is controlled at step 128 to pass at least some of the ions from the multiple-pass drift tube 14, 14', 14" back into the single-pass drift tube 12, 12', 12", 12'''. In the single-pass drift tube 12 illustrated in FIG. 1A, step 128 may be carried out by controlling G1 to the closed or ion-blocking position and controlling G2 to the open or ion-passing position, such that ions traveling through the multiple-pass drift tube 14 pass back into the single-pass drift tube 12, i.e., sequentially via the Y-shaped drift tube segment 36$_2$, the drift tube funnel 32$_4$ and the curved drift tube sub-section 34$_2$. In the single-pass drift tube 12' illustrated in FIG. 1B, step 128 may be carried out by controlling G3 to the closed or ion-blocking position and controlling G4 to the open or ion-passing position, such that ions traveling through the multiple-pass drift tube 14 pass back into the single-pass drift tube 12', i.e., sequentially via the Y-shaped drift tube segment 36$_2$, the drift tube funnel 32$_4$ and the curved branch of the Y-shaped drift tube sub-section 38$_2$. In the single-pass drift tube 12" illustrated in FIG. 1C, step 128 may be carried out by controlling G1, G2 and G3 to their open or ion-passing positions with the electric fields in the drift tube sections 30$_8$ and 35 set to direct ions from the drift tube 34$_2$ to the drift tube sub-section 30$_5$. In the single-pass drift tube 12''' illustrated in FIGS. 1D-1F, step 128 may be carried out by controlling G1 and either G3 or G4, e.g., the openings through the plates 82 and 86 or 88 respectively, to their closed or ion-blocking positions, and controlling G2 and the other of G3 or G4, .e.g., the openings through the plates 84 and 88 or 86 respectively, to their open or ion-passing positions, such that ions traveling through the multiple-pass drift tube 14" pass back into the single-pass drift tube 12''' via the transition region 80.

In one embodiment, ions re-entering the single-pass drift tube 12, 12', 12", 12''' travel, i.e., drift, through the remainder of the single-pass drift tube 12, 12', 12" toward and through the ion outlet 20 under the influence of the electric field established therein where they separate in time in D2 according to the first function of ion mobility. In some alternate embodiments, the open/closed timing of the ion gates G1-G3 (or G1-G4) may be controlled at step 120 such that ions within all ion mobility ranges are passed from the single-pass drift tube 12, 12', 12", 12''' into the multiple-pass drift tube 14, 14', 14", step 126 may be replaced by a step in which the open/closed timing of the ions gates G1-G3 (or G1-G4) are likewise controlled such that ions within all ion mobility ranges travel through the multiple-pass drift tube 14, 14', 14", step 128 may be modified to control the open/closed timing of the ion gates G1-G3 (or G1-G4) such that ions within all ion mobility ranges are passed from the multiple-pass drift tube 14, 14', 14" back into the single-pass drift tube 12, 12', 12", 12''', and one or more additional ion gates within D2, e.g., an ion gate positioned at the ion outlet 20, may be controlled by selectively controlling the open/closed positions of the one or more additional ion gates, e.g., relative to an opening/closing of one or more upstream ion gates, such that only ions within the ion mobility range of interest exit the ion outlet 20 of the single-pass drift tube 12, 12', 12", 12'''.

Ions traveling through the ion outlet 20 are detected at step 130 by the ion detector, and thereafter at step 132 the detected ions are processed by the processor 42 to produce corresponding ion spectral information, e.g., as a function of ion drift time.

In an alternate embodiment, the process 100 illustratively includes a step 134 between steps 120 and 122 such that the single-pass drift tube 12, 12', 12", 12''' and the multiple-pass drift tube 14, 14', 14" operate in parallel as described hereinabove. In one embodiment, step 134 may include steps 102-110 as illustrated in FIG. 3A. In other embodiments, step 134 may include only steps 102-108, and in still other embodiments in which ions are generated or otherwise supplied continually, intermittently or periodically step 134 may include only steps 104-108 or 104-110. In other embodiments still, step 134 may include more, fewer and/or other steps than those just described. In any such embodiments, one or more of the ion gates in the set of ion gates, e.g., G1-G3, may be controlled to one or more intermediate positions between the open and closed positions to direct some of the ions traveling through the single-pass drift 12 into the multiple-pass drift tube 14 while also allowing others of the ions traveling through the single-pass drift tube 12 to travel completely through the single-pass drift tube 12, e.g., to and through the outlet 20 thereof. In such a parallel operating mode, ions supplied by the single or common ion source 18 to the inlet 16 of the single-pass drift tube 12 thus travel in parallel through the single-pass drift tube 12 and also through the combination of the single-pass drift tube 12 and the multiple-pass drift tube 14, with some of the ions traveling directly through the single-pass drift tube 12 to and through the ion outlet 20 and others of the ions traveling through the single-pass drift tube 12, to and through the multiple-pass drift tube 14, then back to and through any remaining section(s) of the single-pass drift tube 12 and exiting the ion outlet 20 of the single-pass drift tube 12.

In the embodiments illustrated in FIGS. 1A-1F, the variously located ion gates, e.g., G1-G3, are disclosed as being controllable in a conventional manner to selectively allow ions to pass therethrough or to selectively block ions from passing therethrough, and/or as being controllable in a conventional manner to selectively allow passage therethrough of only a portion of the ions traveling toward such gates. In some embodiments, one or more, or all, such ion grates are disclosed as being provided in the form of a mesh or grid suitably controlled by one or more conventional DC voltage sources. In some alternate embodiments, one or more, or all, such ion gates are disclosed as being provided in the form of a non-meshed, e.g., grid-less, structure defining an ion passageway therethrough and suitably controlled by one or more conventional DC voltage sources and/or RF voltage sources to selectively block or allow passage of ions therethrough. In still other alternate embodiments, e.g., as illustrated in FIGS. 1D-1F for example, any such ion gates are disclosed as being implemented in, or as part of, one or more ion inlet and/or outlet plates of an ion transition region 80 in which the one or more ion gates are controlled in a conventional manner to selectively control the direction of ion travel within the hybrid ion mobility spectrometer 10'''.

In each of the embodiments 10, 10', 10'', 10''' of the hybrid ion mobility spectrometers illustrated in FIGS. 1A-1F and described above, ion gates are positioned at specific locations therein and are controlled as described to selectively cause ions drifting in an axial direction along and through a drift tube or drift tube segment to either continue to travel in and along the same axial direction, or to divert or redirect the ions to travel in a different direction along and axially through a different drift tube or drift tube section. In some cases, such as with the ion gate pair G1 and G2 in the embodiment 10 illustrated in FIG. 1A and the gate pairs G1, G2 and G3, G4 in the embodiment 10' illustrated in FIG. 1B, the different directions of travel differ by an acute angle, and in other cases, such as with the ion gate pair G1 and G2 in the embodiment 10'' illustrated in FIG. 1C and the ion gates associated with one or more of the plates 82, 84, 86, 88 in the embodiment 10''' illustrated in FIGS. 1D-1F, the different directions of travel are transverse to each other, e.g., normal or approximately normal relative to each other.

In any of the hybrid ion mobility spectrometer embodiments 10, 10', 10'', 10''' illustrated in FIGS. 1A-1F and described above, one or more such ion gates and/or pairs of ion gates may illustratively be replaced by a single, gateless ion steering channel. Advantageously, and as will become apparent from the following description, such an ion steering channel does not operate, as the ion gate embodiments described above, to selectively block and allow passage of ions; rather, such an ion steering channel is controllable, e.g., via application of suitable DC voltages, to selectively steer or guide ions along different directions of ion travel to thereby direct or redirect ions into and through various drift tubes and/or drift tube sections of the spectrometer 10, 10', 10'', 10'''. Ion loss is thus decreased by using one or more such ion steering channels since ions will not be blocked, and thus not lost as with conventional ion gates, and ion concentration in the hybrid ion mobility spectrometers 10, 10', 10'', 10''' will accordingly be increased.

Figure 4A:
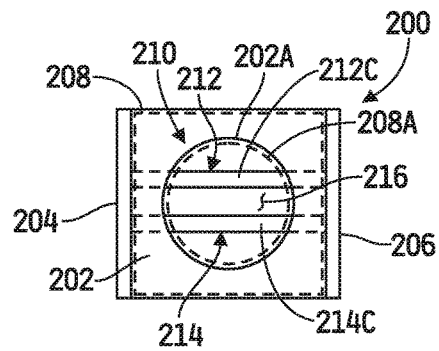
FIG. 4A is a simplified diagram of another embodiment of the transition region of the hybrid ion mobility spectrometer illustrated in FIGS. 1D and 1E.

An example embodiment of an ion steering or guiding structure 200 is illustrated in FIG. 4A, and is provided in the form of an transition region, similar or identical to the transition region 80 illustrated in FIG. 1F, in which an embodiment of an ion steering channel 210 is disposed in place of the ion gates G1-G4. For purposes of this disclosure, the transition region 200 and ion steering channel 210 will be described as replacing the transition region 80 illustrated in FIG. 1E, although it will be understood that the transition region 200 and/or the ion steering channel 210 alone may be implemented as is, or in other forms, in one or more locations in any of the hybrid ion mobility spectrometers 10, 10', 10'', 10''' illustrated in FIGS. 1A-1F and described above. In the embodiment illustrated in FIG. 4A, the transition region 200 illustratively includes a first plate 202 defining an ion passage, e.g., opening, 202A therethrough, which represents an ion inlet to the transition region 200 positioned adjacent to, e.g., the ion outlet of the drift tube funnel $32_2$ (e.g., see FIG. 1E). Another plate 208 opposite to and facing the plate 202 is spaced apart from the plate 202 and illustratively defines an ion passage 208A, e.g., opening, therethrough identical or similar to the opening 202A, which represents an ion outlet of the transition region 200 positioned adjacent to the ion inlet of the drift tube funnel $32_3$. A third plate 204 is positioned between the plate 202 and the plate 208 along one side of the transition region 200, and a fourth plate 206 is positioned opposite the plate 204. The third and fourth plates 204, 206 each define an ion passage, e.g., opening, therethrough which represents an ion inlet/outlet to/of the transition region 200 with the opening defined through the plate 204 positioned adjacent to the ion inlet/outlet of the drift tube sub-section $34_1$ and the opening defined through the plate 206 positioned adjacent to the ion inlet/outlet of the drift tube section $34_2$.

Figure 4B:
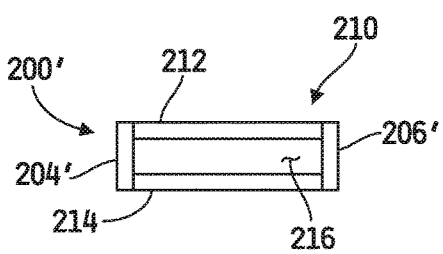
FIG. 4B is a simplified diagram of still another embodiment of the transition region of the hybrid ion mobility spectrometer illustrated in FIGS. 1D and 1E.

Positioned within the transition region 200 illustrated in FIG. 4A is an embodiment of an ion steering channel 210 including planar structures 212, 214 spaced apart from each other by an ion directing channel 216 such that planes defined by each of the planar structures 212, 214 are parallel with each other so that the channel 216 is defined therebetween and such that the planes defined by each of the planar structures 212, 214 are generally normal or approximately normal to planes defined by each of the plates 202, 204, 206, 208. As illustrated in FIG. 4A, the ion steering channel 210 is positioned within the transition region 200 such that the channel 216 defined between the planar structures 212, 214 is illustratively aligned centrally or axially with the ion passages, e.g., 202A, 208A, defined through the plates of the transition region 200 so that ions passing through the openings or ion passages defined through the plates of the transition region 200, e.g., openings or ion passages 202A, 208A, either enter into or exit from the channel 216 in generally in a direction parallel to the planes defined by the opposed inner surfaces of the planar structures 212, 214. An alternate embodiment of an ion steering or guiding structure 200' is illustrated in FIG. 4B, and in the embodiment depicted in FIG. 4B the ion steering or guiding structure 200' illustratively includes the ion steering channel 210 as just described which is illustratively bounded on each side by opposing sidewalls 204', 206' each defining an ion passageway therethrough which is approximately sized identically or complementarily to the channel 216. In some alternate embodiments, the opposing sidewalls 204', 206' may be replaced or supplemented with a similarly or identically configured front wall and/or a similarly or identically configured rear wall.

In some embodiments, the planar structures 212, 214 of the ion channel 210 are each illustratively provided in the form of a conventional circuit board having a plurality of electrically conductive surfaces or pads formed in a conventional manner on an inner, major surface thereof and each electrically connectable to a suitable voltage source, e.g., a DC or other voltage source. The electrically conductive surfaces or pads formed on the circuit board 212 are illustratively identical and complementary to those formed on the circuit board 214 such that the electrically conductive surfaces or pads formed on the circuit board 212 are juxtaposed with corresponding ones of the electrically conductive surfaces or pads formed on the circuit board 214 when the inner surfaces of the circuit boards 212, 214 are spaced apart to define the channel 216 as illustrated in FIGS. 4A and 4B. The circuit boards 212, 214 may illustratively be conventional printed circuit boards ("PCB's") or other conventional circuit boards formed of one or more conventional electrically insulating or non-conductive materials, e.g., fiber-reinforced or paper-reinforced epoxy resin, alumina, one or more ceramic materials, etc., and the electrically conductive surfaces or pads may be formed of one or more conventional electrically conductive materials, e.g., copper, aluminum and/or other metallic or non-metallic but electrically conductive materials. The circuit boards 212, 214 may illustratively use through-hole, surface-mounting and/or other structures and techniques for mounting electrical components and/or connecting electrical power sources thereto.

Figure 5:
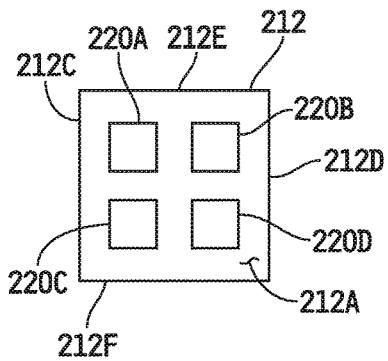
FIG. 5 is a bottom plan view of one of the planar members of either of the embodiments illustrated in FIGS. 4A and 4B.
Figure 6:
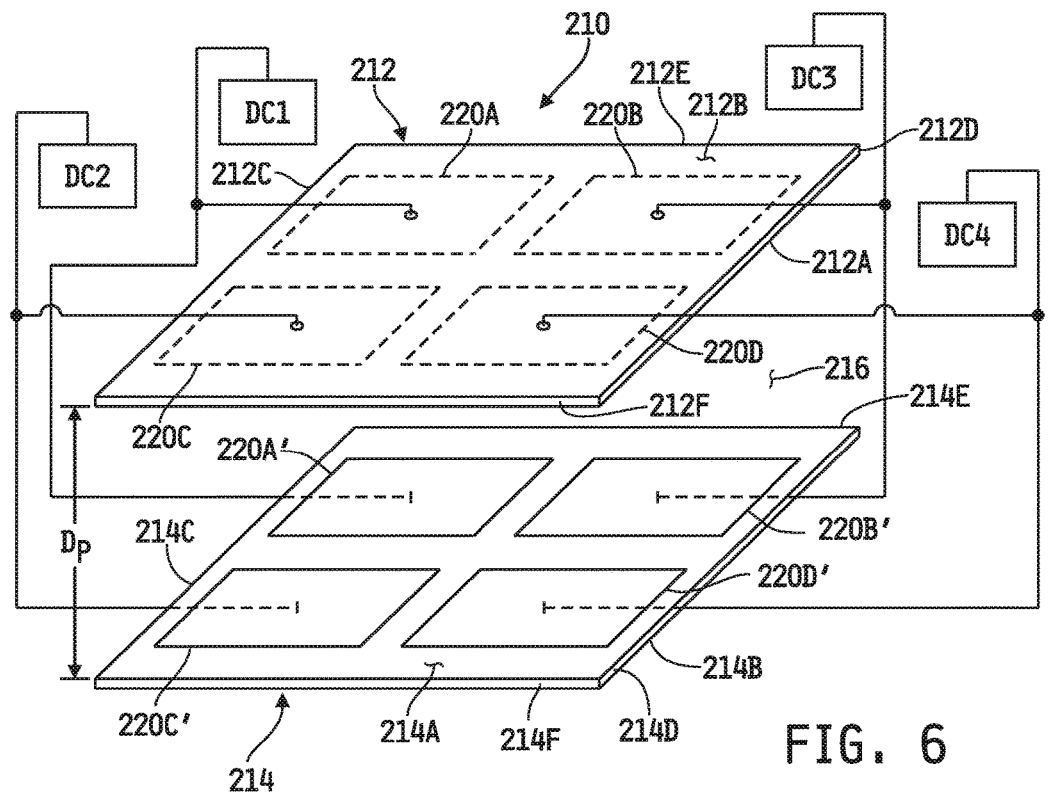
FIG. 6 is a simplified perspective view of an embodiment of an ion steering channel that may be implemented in any of the hybrid ion mobility spectrometers illustrated in FIGS. 1A-1F.

Referring now to FIG. 5, an example embodiment is shown of the inner, major surface 212A one of the planar circuit boards 212 of FIGS. 4A and 4B upon which a pattern of 4 substantially identical and spaced apart electrically conductive pads 220A-220D are formed. The inner, major surface 214A of the planar circuit board 214 has an identical pattern of 4 electrically conductive pads 220A'-220D' formed thereon, and the electrically conductive pads 220A-220D are juxtaposed over corresponding ones of the electrically conductive pads 220A'-220D' when the inner, major surface 212A of the circuit board 212 is spaced apart from and generally parallel with the inner, major surface 214A of the circuit board 214 so that the inner, major surfaces 212A and 214A define the channel 216 therebetween as illustrated in FIG. 6. In one embodiment, the distance, $D_P$, of the channel or space 216 defined between the inner surfaces 212A, 214A of the circuit boards 212, 214 is approximately 5 cm, although in other embodiments the distance $D_P$ may be greater or lesser than 5 cm, and it will be understood that the distance $D_P$ will depend, at least in part, on the particular application in which the ion steering channel 210 is implemented.

Referring now to FIG. 6, the planar circuit board 212 is shown illustratively spaced apart from the planar circuit board 214 such that upstream edges 212C and 214C of the respective circuit boards 212, 214 are aligned, as are downstream edges 212D, 214D and opposing side edges 212E, 214E and 212F, 214F. The terms "upstream" and "downstream" illustratively refer to the direction of ion travel such that, in the embodiment illustrated in FIG. 4A, for example, the aligned edges 212C, 214C are positioned in contact with or adjacent to the plate 202 such that the channel 216 is axially aligned with the opening 202A, and the aligned edges 212D, 214D are positioned in contact with or adjacent to the plate 208 such that the channel 216 is axially aligned with the opening 208A. In any case, the major surface 212B of the planar circuit board 212 opposite the inner, major surface 212A will illustratively be referred to as the outer surface of the planar circuit board 212, and the major surface 214B of the planar circuit board 214 opposite the inner, major surface 214A will illustratively be referred to as the outer surface of the planar circuit board 214.

In the embodiment illustrated in FIG. 6, a first DC voltage source DC1 is electrically connected to each of the juxtaposed electrically conductive pads 220A, 220A' such that the potential at both pads 220A, 220A' is the potential produced by DC1, a second DC voltage source DC2 is electrically connected to each of the juxtaposed electrically conductive pads 220C, 220C' such that the potential at both pads 220C, 220C' is the potential produced by DC2, a third DC voltage source DC3 is electrically connected to each of the juxtaposed electrically conductive pads 220B, 220B' such that the potential at both pads 220B, 220B' is the potential produced by DC3, and a fourth DC voltage source DC4 is electrically connected to each of the juxtaposed electrically conductive pads 220D, 220D' such that the potential at both pads 220D, 220D' is the potential produced by DC4. In some embodiments, one or more conventional electrical components, e.g., resistors or other components, may be interconnected between one or more of the voltage sources DC1-DC4 and one or more of the corresponding electrically conductive pads 220A-220D and 220A'-220D' and/or between two or more, and/or two or opposed pairs, of the electrically conductive pads 220A-220D and 220A'-220D'. In the illustrated embodiment, each of the DC voltage sources DC1-DC4 is independently controlled, e.g., via manually or via the processor 42, although in alternate embodiments two or more of the DC voltage sources DC1-DC4 may be controlled together as a group. In any case, it will be understood that although the voltage sources DC1-DC4 are illustrated and disclosed as being DC voltage sources, this disclosure contemplates other embodiments in which one or more of the voltage sources DC1-DC4 is or includes an AC voltage source such as, for example, an RF voltage source suitably coupled, e.g., capacitively, via conventional electrical components to corresponding ones or pairs of the electrically conductive pads 220A-220D and 220A'-220D'.

Figure 7A:
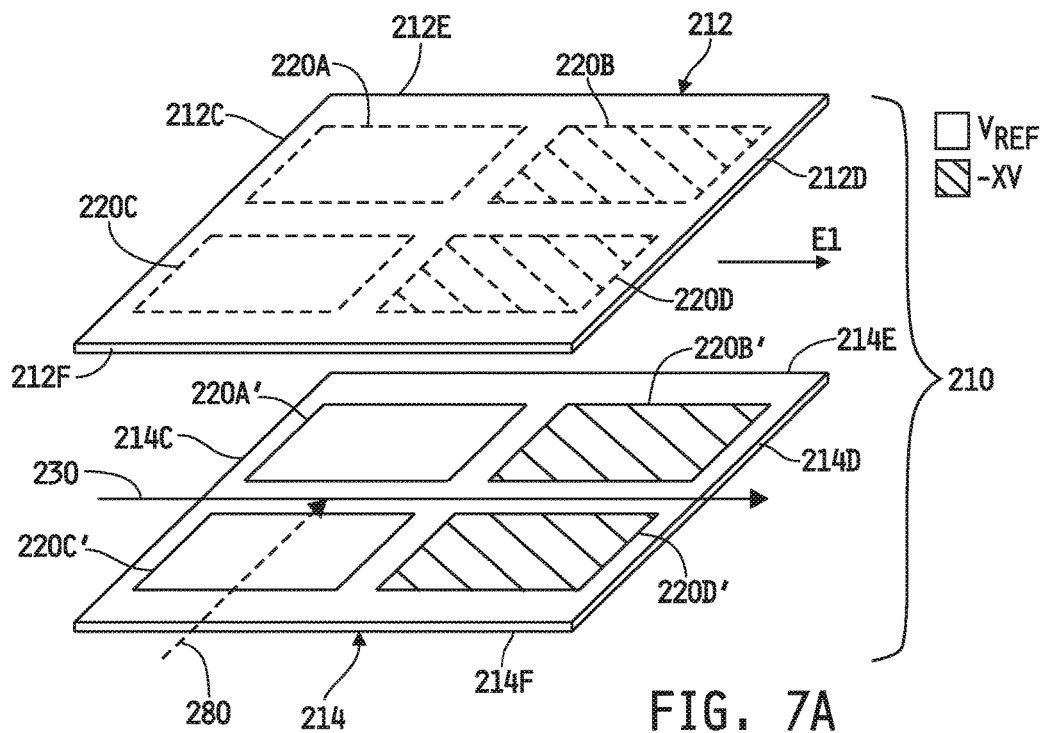
FIG. 7A is a simplified perspective diagram illustrating an example operating mode of the ion steering channel illustrated in FIG. 6.
Figure 7B:
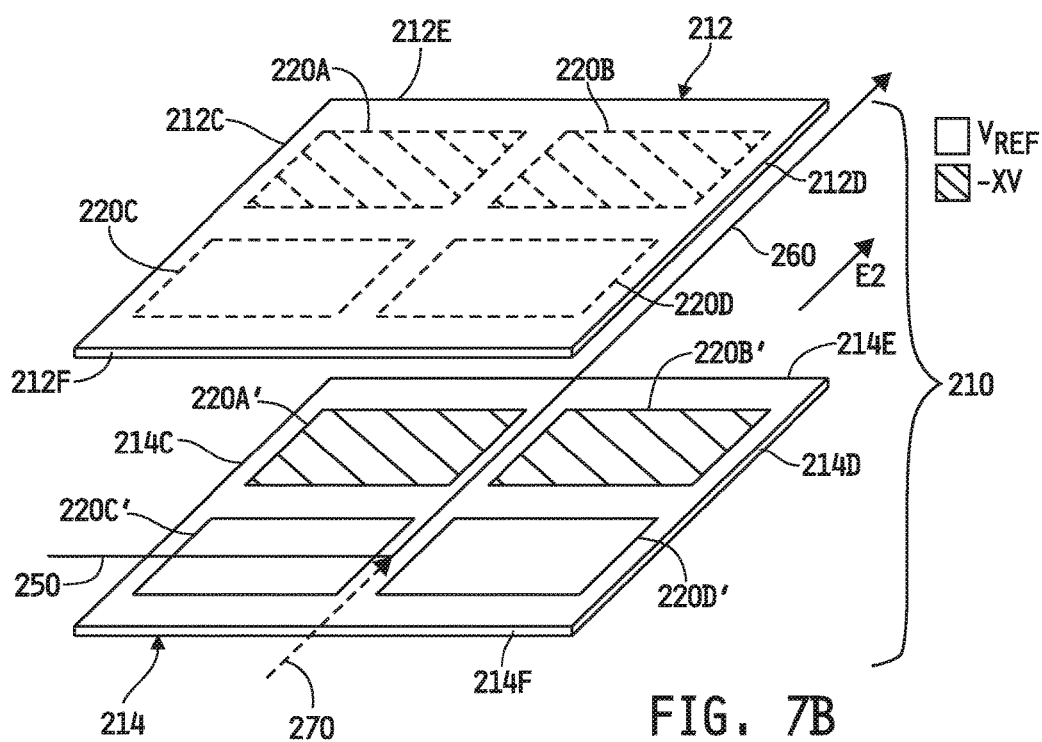
FIG. 7B is a simplified perspective diagram illustrating another example operating mode of the ion steering channel illustrated in FIG. 6.

Referring now to FIGS. 7A and 7B, operation of the ion steering channel 210 illustrated in FIG. 6 will be described as implemented in the form of the ion steering or guiding structure 200 or 200' in place of the ion transition region 80 of the ion mobility spectrometer 10''' illustrated in FIGS. 1D-1F. It will be understood, however, that the ion steering channel 210 may alternatively or additionally be implemented in place of one or more ion gates in one or more of the other embodiments 10, 10', 10'' of the ion mobility spectrometer described above. In any case, the DC voltage sources DC1-DC4 are omitted in FIGS. 7A and 7B for clarity of illustration, and instead the various DC voltages produced thereby and applied to the connected pairs of electrically conductive pads 220A/220A', 220B/220B', 220C/220C' and 220D/220D' are represented graphically. Referring specifically to FIG. 7A, the ion steering channel 210 is shown in a state in which a reference potential, $V_{REF}$, is applied by each of DC1 and DC2 to the electrically conductive pad pairs 220A/220A' and 220C/220C' respectively, and a potential –XV, less than $V_{REF}$, is applied by each of DC3 and DC4 to the electrically conductive pad pairs 220B/220B' and 220D/220D' respectively. Illustratively, $V_{REF}$ may be any positive or negative voltage, or may be zero volts, e.g., ground potential, and –XV may be any voltage, positive, negative or zero voltage that is less than $V_{REF}$ so as to establish an electric field E1 which is parallel with the sides 212E, 214E and 212F, 214F of the circuit boards 212, 214 and which extends in a direction from and generally normal to the upstream edges 212C, 214C toward and normal to the downstream edges 212D, 214D of the circuit boards 212, 214 as depicted in FIG. 7A. With the electric field, E1, established as illustrated in FIG. 7A, ions 230 drifting through the drift tube segment $32_2$ of the single-pass drift tube 12''' enter the channel 216 between the upstream edges 212C, 214C and are steered or guided (or directed) by the electric field, E1 in a direction generally parallel with the ion travel axis 72 of the drift tube 12''', and such ions thus pass into the drift tube segment $32_3$ of the single-pass drift tube 12''' as described above with respect to FIGS. 1D-1F.

Referring now to FIG. 7B, when it is desired to direct ions from the single-pass drift tube 12''' into the multiple-pass drift tube 14", as also described above with respect to FIGS. 1D-1F, the reference potential, $V_{REF}$, is applied by each of DC2 and DC4 to the electrically conductive pad pairs 220C/220C' and 220D/220D' respectively, and a potential −XV, less than $V_{REF}$, is applied by each of DC1 and DC3 to the electrically conductive pad pairs 220A/220A' and 220B/220B' respectively, so as to establish an electric field E2 which is parallel with the upstream edges 212C, 214C and the downstream edges 212D, 214D of the circuit boards 212, 214, and which extends in a direction from and generally normal to the sides 212F, 212F toward and normal to the sides 212E, 214E of the circuit boards as depicted in FIG. 7B. With the electric field, E2, established as illustrated in FIG. 7B, ions 250 drifting through the drift tube segment $32_2$ in the direction generally parallel with the ion travel axis 72 of the drift tube 12''' and entering the channel 216 through the upstream edges 212C, 214C of the ion steering channel 210 will be steered or guided (or directed) by the electric field, E2, so as to be diverted to travel in a direction from and generally normal to the sides 212F, 212F toward and normal to the sides 212E, 214E of the circuit boards and thus into the drift tube segment $34_1$ of the multiple-pass drift tube 14" as described above with respect to FIGS. 1D-1F. Thus, the ions drifting through the drift tube segment $32_2$ in the direction generally parallel with the ion travel axis 72 of the drift tube 12''' are diverted by E2 to travel in a direction that is generally normal to the ion travel axis 72. Thereafter, as long as the voltage sources DC1-DC4 continue to be controlled so as to maintain the electric field E2, ions 270 drifting through the multiple-pass drift tube 14" in a clockwise direction and generally parallel with the ion travel axis 70 of the multiple-pass drift tube 14" (as viewed in FIG. 1D) will enter the channel 216 from the drift tube segment $34_2$ at the sides 212F, 214F of the circuit boards 212, 214 and be steered or guided (or directed) by the electric field, E2, in a direction parallel with the ion travel axis 70 of the multiple-pass drift tube 14" and thus back into the drift tube segment $34_1$ as described above with respect to FIGS. 1D-1F.

After a desired number of traversals by the ions through the multiple-pass drift tube 14", the reference potential, $V_{REF}$ or other suitable reference potential, is applied by each of DC1 and DC2 to the electrically conductive pad pairs 220A/220A' and 220C/220C' respectively, and the potential −XV or other suitable potential less than $V_{REF}$, is applied by each of DC3 and DC4 to the electrically conductive pad pairs 220B/220B' and 220D/220D' respectively, so as to reestablish the electric field E1, or to establish another electric field in the same direction as E1, such that ions 280 drifting through the drift tube segment $34_2$ of the multiple-pass drift tube 14" and into the ion steering channel 210 will be steered or guided (or directed) by such an electric field in the downstream direction of the ion travel axis 72 of the single-pass drift tube 12''' thus into the drift tube segment $32_3$ of the single-pass drift tube 12''' as described above with respect to FIGS. 1D-1F. Thus, the ions 280 drifting through the drift tube segment $34_2$ of the multiple-pass drift tube 14" in the direction generally parallel with the ion travel axis 70 of the multiple-pass drift tube 14" are diverted by E2 to travel in a direction that is generally normal to the ion travel axis 70 as illustrated in FIG. 7A.

Figure 8:
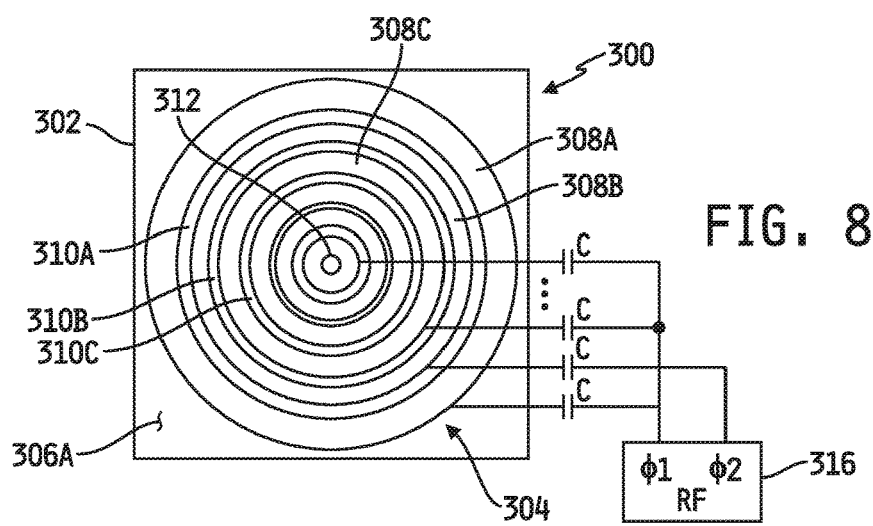
FIG. 8 is a simplified elevational diagram illustrating an embodiment of an ion carpet that may be implemented in any of the hybrid ion mobility spectrometers illustrated in FIGS. 1A-1F.

In each of the embodiments 10, 10', 10", 10''' of the hybrid ion mobility spectrometer illustrated in FIGS. 1A-1F, ion funnels, e.g., in the form of ion funnels $32_1$-$32_{11}$ and/or drift tube sections 50, are illustratively implemented in and along the single-pass drift tube 12, 12', 12", 12''' as well as in and along the multiple-pass drift tube 14, 14', 14". In some alternate embodiments, including any such embodiments which include one or more ion steering or guiding structures 200 and/or 200' and/or ion steering channels 210, one or more such ion funnels may be replaced by one or more conventional ion carpets of the general form illustrated in FIG. 8. Referring to FIG. 8, the illustrated ion carpet 300 is provided in the form of a planar structure 302, e.g., a circuit board or other electrically insulating or non-conductive plate, having a ring structure 304 with multiple, axially aligned, electrically conductive rings with progressively decreasing ring diameters formed on one major surface 306A thereof. In the embodiment illustrated in FIG. 8, the ring structure 304 includes a number of axially aligned, electrically conductive, concentric rings 308A, 308B, 308C . . . formed on one major surface 306 thereof with each successive ring 308A, 308B, 308C . . . reduced in diameter relative to the previous ring. Adjacent rings 308A, 308B, 308C . . . are radially separated from each other by electrically insulating or non-conductive ring areas 310A, 310B, 310C . . . of the planar structure 302. In embodiments in which the planar member 302 is a circuit board, the electrically conductive rings 308A, 308B, 308C are illustratively applied in a conventional manner on and to the major surface 306A of the circuit board 302 in the form of electrically conductive films or traces, e.g., copper, aluminum and/or other electrically conductive material. An ion passageway 312, e.g., in the form of a through-hole, having a central axis in common with each of the number of electrically conductive rings 308A, 308B, 308C . . . and electrically insulating or non-conductive areas 310A, 310B, 310C . . . of the planar structure 302 is defined through the planar structure 302. In the illustrated embodiment, six such electrically conductive rings are shown, although it will be understood that the planar structure 302 may include more or fewer such rings. Moreover, it will be understood that whereas the electrically conductive rings 308A, 308B, 308C . . . and electrically insulating or non-conductive areas 310A, 310B, 310C . . . of the planar structure 302 are illustrated in FIG. 8 as being concentric structures, alternate embodiments are contemplated in which such structures are non-concentric but closed structures. In any case, a conventional AC voltage source, e.g., a conventional RF voltage source, 316 is coupled through a capacitor network to each of the electrically conductive rings 308A, 308B, 308C . . . such that an RF voltage of a first phase, $\phi_1$, is applied to odd-numbered (or even-numbered) ones of the rings 308A, 308B, 308C . . . and the same RF voltage of a second phase, $\phi_2$, is applied to even-numbered (or odd-numbered) ones of the rings 308A, 308B, 308C . . . . In some embodiments, $\phi_1$-$\phi_2$ (or $\phi_2$-$\phi_1$)=180 degrees such that an opposite phase RF voltage is applied to adjacent ones of the rings 308A, 308B, 308C . . . of the ion carpet 300 as illustrated in FIG. 8. Generally, the ion carpet 300 illustratively operates functionally the same as ion funnels in that ions travelling toward the major surface 306A of the ion carpet 300 are focused radially inwardly by the RF voltages applied to the rings 308A, 308B, 308C . . . toward and through the central ion passageway 312. Accordingly, the ion carpet 300 may be used in place of any ion funnel structure described in connection with any of the embodiments 10, 10', 10", 10''' of the hybrid ion mobility spectrometer illustrated in FIGS. 1A-1F.

Figure 9:
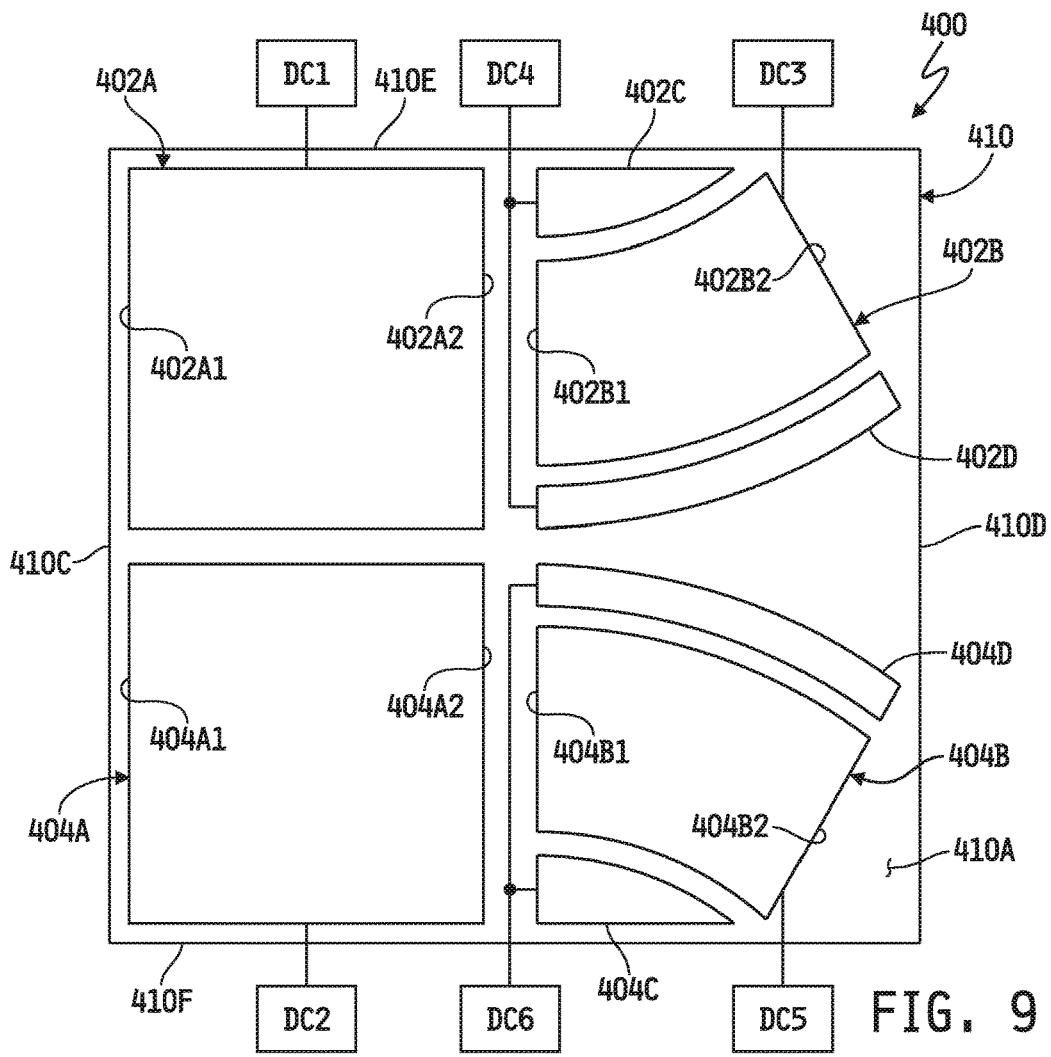
FIG. 9 is a simplified elevational diagram illustrating an embodiment of one of two planar members forming another embodiment of an ion steering channel that may be implemented in any of the hybrid ion mobility spectrometers illustrated in FIGS. 1A-1F.

Referring now to FIG. 9, a portion of another embodiment of an ion steering or guiding structure 400 is shown in the form of an electrically insulating or non-conductive planar member 410, e.g., a printed circuit board or the like, having an inner, major surface 410A upon which a number of electrically conductive pads are formed. The planar circuit board 410 illustratively includes an upstream edge 410C, a downstream edge 410D opposite the upstream edge 410C and two opposing side edges 410E, 410F joining the upstream and downstream edges 410C, 410D, wherein the edges 410C, 410D, 410E, 410F surround the inner, major surface 410A and an opposite outer, major surface 4106 (see, e.g., FIG. 14), and wherein the terms "upstream" and "downstream" are as described above. In the illustrated embodiment, the planar circuit board has two sets of two substantially identical and spaced apart electrically conductive pads 402A and 404A are formed thereon. Along the upstream edge 410C and spaced-apart between the side edges 410E, 410F a pair of square or rectangular electrically conductive pads 402A, 404A are formed on the inner, major surface 410A of the planar circuit board 410, and along the downstream edge 410D and spaced-apart between the side edges 410E, 410F a pair of generally arcuate-shaped electrically conductive pads 402B, 404B are formed on the inner, major surface 410A. Each square or rectangular pad 402A, 404A has a substantially planar upstream edge 402A1, 404A1 respectively that is substantially parallel with the upstream edge 410C of the planar circuit board 410, and a substantially planar downstream edge 402A2, 404A2 respectively that is substantially parallel with the planar upstream edge 402A1, 404A1 respectively. Each arcuate-shaped pad 402B, 404B, in contrast, has a generally planar upstream edge 402B1, 404B1 respectively that is generally parallel with and spaced apart from the downstream edge 402A2, 404A2 of the respective square or rectangular pad 402A, 404A, and a generally planar downstream edge 402B2, 404B2 respectively that illustratively forms an acute angle with the respective upstream edge 402B1, 404B1 such that the arcuate-shaped pads 402B, 404B generally diverge from one another as the pads 402B, 404B extend generally toward the downstream edge 410D of the planar circuit board 410. Each of the actuate shaped pads 402B, 404B is flanked along opposing side edges by electrically conductive pads 402C, 402D and 404C, 404D respectively, each of which defines an arcuate-shaped side edge that faces a respectively arcuate-shaped side edge of the electrically conductive pads 402B, 404B such that all such opposing arcuate shaped side edges are spaced-apart equidistantly along the lengths of the opposing sides of the electrically conductive pads 402B, 404B.

Like the ion steering and guiding structure 210 illustrated in FIG. 6, the steering or guiding structure 400 illustratively includes a second planar circuit board 410 configured identically to the planar circuit board 410 just described and having identical spaced-apart electrically conductive pads 402A-402D, 404A-404D formed thereon. All such electrically conductive pads 402A-402D, 404A-404D of the two planar circuit boards 410 are juxtaposed over corresponding ones of the electrically conductive pads 402A-402D, 404A-404D when the inner, major surfaces 410A of the two identical circuit boards 410 are spaced apart from and generally parallel with each other so that the inner, major surfaces 212A and 214A define a channel, e.g., similar or identical to the channel 216, therebetween as illustrated in FIG. 6 and described above. In the description that follows, it will be understood that an ion steering channel formed with the planar circuit board 410 illustrated in FIG. 9 will necessarily include such a second, identically configured planar circuit board 410, and that although only a single one of the planar circuit boards 410 is illustrated in FIGS. 9 and 10A-10B, such a second planar circuit board 410 will be connected to voltage sources identically as shown and described with respect to the illustrated planar circuit board 410 and that the functional operation, e.g., relating to ion steering, of the ion steering channel formed with the illustrated planar circuit board 410 will generally take place in and through the channel formed between the illustrated circuit board 410 and such a second planar circuit board 410.

In the embodiment illustrated in FIG. 9, a first DC voltage source DC1 is electrically connected to each of the juxtaposed electrically conductive pads 402A (of the illustrated planar circuit board 410 and a second, identically configured planar circuit board spaced apart therefrom) such that the potential at both pads 402A is the potential produced by DC1, a second DC voltage source DC2 is electrically connected to each of the juxtaposed electrically conductive pads 404A such that the potential at both pads 404A is the potential produced by DC2, a third DC voltage source DC3 is electrically connected to each of the juxtaposed electrically conductive pads 402B such that the potential at both pads 402B is the potential produced by DC3, a fourth DC voltage source DC4 is electrically connected to each of the juxtaposed electrically conductive pad pairs 402C, 402D such that the potential at both pairs of pads 402C, 402D is the potential produced by DC4, a fifth DC voltage source DC5 is electrically connected to each of the juxtaposed electrically conductive pads 404B such that the potential at both pads 404B is the potential produced by DC5, and a sixth DC voltage source DC6 is electrically connected to each of the juxtaposed electrically conductive pad pairs 404C, 404D such that the potential at both pairs of pads 404C, 404D is the potential produced by DC6. In some embodiments, one or more conventional electrical components, e.g., resistors or other components, may be interconnected between one or more of the voltage sources DC1-DC6 and one or more of the corresponding electrically conductive pads 402A-402D, 404A-404D and/or between two or more, and/or two or opposed pairs, of the electrically conductive pads 402A-402D, 404A-404D. In the illustrated embodiment, each of the DC voltage sources DC1-DC6 is independently controlled, e.g., via manually or via the processor 42, although in alternate embodiments two or more of the DC voltage sources DC1-DC6 may be controlled together as a group. In any case, it will be understood that although the voltage sources DC1-DC6 are illustrated and disclosed as being DC voltage sources, this disclosure contemplates other embodiments in which one or more of the voltage sources DC1-DC6 is or includes an AC voltage source such as, for example, an RF voltage source suitably coupled, e.g., capacitively, via conventional electrical components to corresponding ones or pairs of the electrically conductive pads 402A-402D, 404A-404D.

Figure 10A:
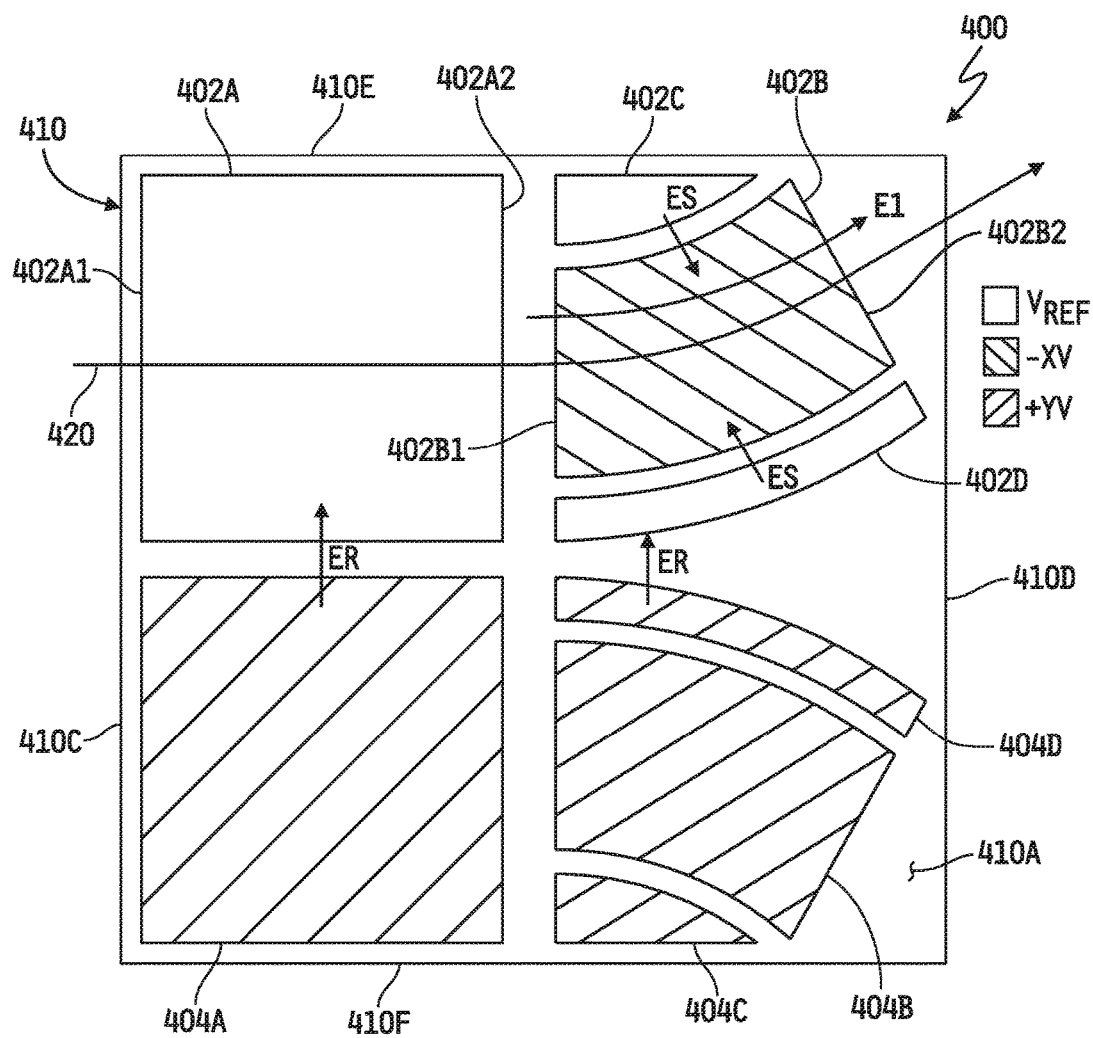
FIG. 10A is a simplified elevational diagram illustrating an example operating mode of the ion steering channel partially illustrated in FIG. 9.
Figure 10B:
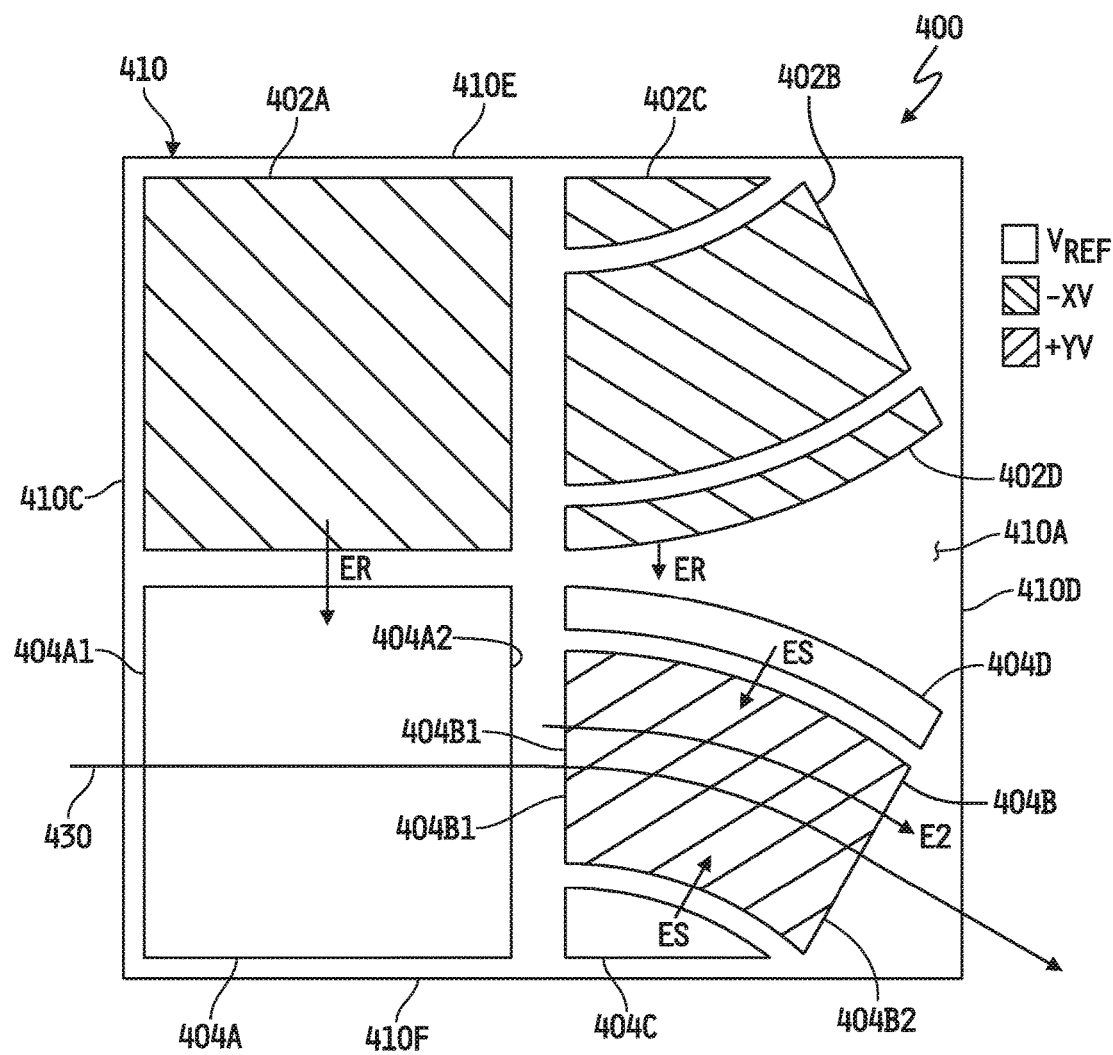
FIG. 10B is a simplified perspective diagram illustrating another example operating mode of the ion steering channel partially illustrated in FIG. 9.

Referring now to FIGS. 10A and 10B, operation of an ion steering channel 400, formed by the planar circuit board 410 spaced apart from a second, identical planar circuit board 410 with corresponding ones of the electrically conductive pads 402A-402D, 404A-404D of each circuit board 410 juxtaposed with each other, will be described. The DC voltage sources DC1-DC6 are omitted in FIGS. 10A and 10B for clarity of illustration, and instead the various DC voltages produced thereby and applied to the connected pairs of electrically conductive pads 402A-402D, 404A-404D are represented graphically. Referring specifically now to FIG. 10A, the ion steering channel 400 is shown in a state in which a reference potential, VREF, is applied by DC1 to the electrically conductive pad pairs 402A and by DC4 to the electrically conductive pad pairs 402C and 402D, and a potential −XV, less than VREF, is applied by DC3 to the electrically conductive pad pairs 402B. Illustratively, VREF may be any positive or negative voltage, or may be zero volts, e.g., ground potential, and −XV may be any voltage, positive, negative or zero voltage that is less than VREF so as to establish an electric field E1 which is normal to the planar edges 402A1, 402A2, 402B1, 402B2 of the electrically conductive pad pairs 402A, 402B respectively and which thus follows the arcuate shape of the electrically conductive pad pairs 402B as shown. Because the potential applied by DC4 to the electrically conductive pad pairs 402C and 402D is also VREF, additional electric fields, ES, are thus established normal to the arcuate side edges of the electrically conductive pad pairs 402B in the direction of the electrically conductive pad pairs 402B to thereby confine ions to the arcuate path defined by the electrically conductive pad pairs 402B such that the ions entering the ion steering channel 400 at and in a direction normal to the upstream edges 410C travel linearly across the electrically conductive pad pairs 402A and then across the electrically conductive pad pairs 402B generally in the arcuate direction defined by the arcuate electric field E1.

Referring specifically now to FIG. 10B, the ion steering channel 400 is shown in a state in which a reference potential, VREF, is applied by DC2 to the electrically conductive pad pairs 404A and by DC6 to the electrically conductive pad pairs 404C and 404D, and a potential −XV, less than VREF, is applied by DC5 to the electrically conductive pad pairs 404B. Illustratively, VREF may be any positive or negative voltage, or may be zero volts, e.g., ground potential, and −XV may be any voltage, positive, negative or zero voltage that is less than VREF so as to establish an electric field E2 which is normal to the planar edges 404A1, 404A2, 404B1, 404B2 of the electrically conductive pad pairs 404A, 404B respectively and which thus follows the arcuate shape of the electrically conductive pad pairs 404B as shown. Because the potential applied by DC6 to the electrically conductive pad pairs 404C and 404D is also VREF, additional electric fields, ES, are thus established normal to the arcuate side edges of the electrically conductive pad pairs 404B in the direction of the electrically conductive pad pairs 404B to thereby confine ions to the arcuate path defined by the electrically conductive pad pairs 404B such that the ions entering the ion steering channel 400 at and in a direction normal to the upstream edges 410C travel linearly across the electrically conductive pad pairs 404A and then across the electrically conductive pad pairs 404B generally in the arcuate direction defined by the arcuate electric field E2.

In the embodiment shown in FIG. 10A, a potential +YV is illustratively applied by DC2, DC5 and DC6 to the electrically conductive pad pairs 404A, 404B and 404C/404D respectively, and in the embodiment shown in FIG. 10B the potential +YV is illustratively applied by DC1, DC3 and DC4 to the electrically conductive pad pairs 402A, 402B and 402C/402D respectively. Illustratively, +YV is selected to establish a repulsive electric field ER of sufficient strength to confine ions entering the ion steering channel 400 at and in a direction normal to the upstream edges 410C to the electrically conductive pad pairs 402A and 404B respectively so that such ions will not be lost and will be directed by the electric fields E1 and E2 respectively to follow the arcuate path established thereby. In some alternate embodiments, DC2, DC5 and DC6 may instead apply VREF to the electrically conductive pad pairs 404A, 404B and 404C/404D respectively and/or DC1, DC3 and DC4 may instead apply VREF to the electrically conductive pad pairs 402A, 402B and 402C/402D respectively.

As illustrated in FIGS. 10A and 10B, the ion steering channel 400 is selectively operable, via control of the voltage sources DC1-DC6, to direct ions entering the ion steering channel 400 at and in a direction normal to the upstream edges 410C along the arcuate path established by E1 or E2, wherein the ion outlets of the arcuate paths diverge from each other. In some embodiments, the ion steering channel 400 may be used in place of the ion gate pairs in any of the diverging drift tube segments of either of the embodiments 10, 10' illustrated in FIGS. 1A and 1B, e.g., in place of the ion gate pair G1, G2 in the drift tube segment $36_2$ of the hybrid ion mobility spectrometer 10 illustrated in FIG. 1A, in place of the ion gate pair G1, G2 in the drift tube segment $38_1$ of the hybrid ion mobility spectrometer 10' illustrated in FIG. 1B and/or in place of the ion gate pair G3, G4 in the drift tube segment $36_2$ of the hybrid ion mobility spectrometer 10'. Alternatively or additionally, the ion steering channel 400 illustrated in FIGS. 9-10B may be rotated 180 degrees such that ions enter the ion steering channel 400 at and in a direction normal to the edges 410D and the rotated ion steering channel 400 may be used in place of the ion gate G3 in the drift tube segment $36_1$ of the hybrid ion mobility spectrometer 10 illustrated in FIG. 1A. In any such embodiment, the electrically conductive arcuate pad pairs 402B-402D, 404B-404D are illustratively shaped such that the curvatures of such pad pairs match and align with the curvatures of the diverging paths of the drift tube segments $36_2$, $38_1$ and/or of the converging paths of the drift tube segment $36_1$.

In some embodiments in which either of the ion steering channel 210 and/or the ion steering channel 400 is implemented, it may be desirable to, under some operating conditions, selectively confine ion travel or passage to only one side or the other of the channel 210, 400 and, under other operating conditions, to allow for ion travel through both sides of the channel 210, 400. As used herein, "through one side of the channel" will be understood to mean ion travel through the channel 210, 400 along one axially or transversely aligned set of pairs of electrically conductive pads, e.g., axially along the aligned set of the electrically conductive pad pairs 402A and 402B under the influence of the electric field E1 as illustrated in FIG. 10A, axially along the aligned set of the electrically conductive pad pairs 404A and 404B under the influence of the electric field E2 as illustrated in FIG. 10B, transversely along the aligned set of electrically conductive pad pairs 220C, 220C' and 220A, 220A' as depicted by the dashed line 280 in FIG. 7A, and axially along the aligned set of electrically conductive pad pairs 220C, 220C' and 220D, 220D' as depicted by the solid line 250 in FIG. 7B. Similarly, "through both sides of the channel" will be understood to mean ion travel through the channel 210, 400 along both axially or transversely aligned sets of pairs of electrically conductive pads, e.g., axially along the aligned sets of electrically conductive pad pairs 220A, 220A' and 220B, 220B' and, at the same time, axially along the aligned sets of electrically conductive pad pairs 220C, 220C' and 220D, 220D' as depicted by the solid line 230 in FIG. 7A, and transversely along the aligned sets of electrically conductive pad pairs 220C, 220C' and 220A, 220A' and, at the same time, transversely along the aligned sets of electrically conductive pad pairs 220D, 220D' and 220B, 220B' as depicted by the dashed line 270 in FIG. 7B.

Figure 11:
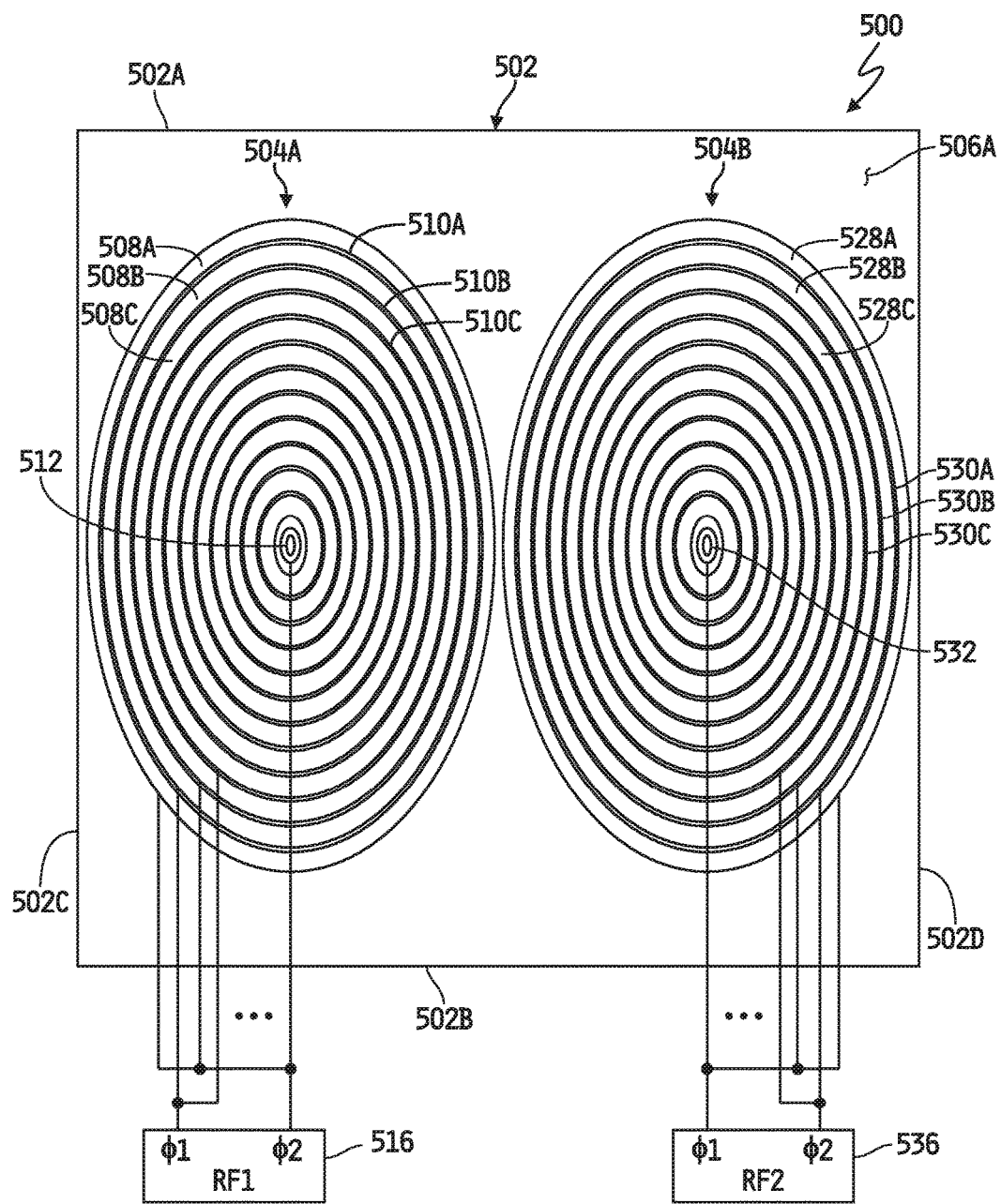
FIG. 11 is a simplified elevational diagram illustrating another embodiment of an ion carpet that may be implemented in any of the hybrid ion mobility spectrometers illustrated in FIGS. 1A-1F.

In some such embodiments, selective guidance or steering of ion travel or passage through only one side or the other, or through both sides, of an ion steering channel 210, 400 is accomplished with a dual-passage or ion carpet, one example embodiment of which is illustrated by example in FIG. 11. Referring now to FIG. 11, the illustrated dual-passage ion carpet 500 is provided in the form of a planar structure 502, e.g., a circuit board or other electrically insulating or non-conductive plate, having side-by-side ring structure 504A, 504B each with multiple, axially aligned and progressively smaller electrically conductive rings formed on one major surface 506A thereof. In the illustrated embodiment, the planar circuit board 502 illustratively has a top edge 502A, a bottom edge 502B opposite the top edge 502A with the top and bottom edges 502A, 502B joined by opposing edges 502C, 502D. The major surface 506A of the circuit board is defined between the edges 502A-502D on one side of the circuit board 502, and another major surface 506B (see, e.g., FIGS. 112A-13) is defined between the edges 502A-502D opposite the major surface 506A.

In the embodiment illustrated in FIG. 11, the ring structure 504A includes a number of axially aligned, electrically conductive, elliptical rings 508A, 508B, 508C . . . formed on the major surface 506A of the circuit board 502 with each successive ring 508A, 508B, 508C . . . reduced in length of both major and minor axes relative to the previous ring. Adjacent rings 508A, 508B, 508C . . . are radially separated from each other by electrically insulating or non-conductive ring areas 510A, 510B, 510C . . . of the planar structure 502. An ion passageway 512, e.g., in the form of a through-hole, having a central axis in common with each of the number of electrically conductive rings 508A, 508B, 508C . . . and electrically insulating or non-conductive areas 510A, 510B, 510C . . . of the planar structure 502 is defined through the planar structure 502. Illustratively, the ring structure 504A is positioned on the major surface 506A of the circuit board 502 such that the ion passageway 512 aligns with the channel 216 or space defined between the opposed circuit boards of an ion steering channel 210, 400 and is also centrally aligned with axially or transversely aligned with sets of pairs of electrically conductive pads formed on one side, e.g., a left side, of the ion steering channel 210, 400 when the ion carpet 500 is operatively mounted to or operatively positioned adjacent to the ion steering channel 210, 400, e.g., such that the ion passageway 512 bisects or approximately bisects the channel 216 and bisects or approximately bisects the axially or transversely aligned sets of pairs of electrically conductive pads on one side of the ion steering channel. In the illustrated embodiment, 13 such electrically conductive rings are shown, although it will be understood that the planar structure 502 may include more or fewer such rings. Moreover, it will be understood that whereas the electrically conductive rings 508A, 508B, 508C . . . and electrically insulating or non-conductive areas 510A, 510B, 510C . . . of the planar structure 502 are illustrated in FIG. 11 as being elliptical structures, alternate embodiments are contemplated in which such structures are concentric or other closed structures. In any case, a conventional AC voltage source 516, e.g., a conventional RF voltage source, is operatively coupled through a capacitor network to each of the electrically conductive rings 508A, 508B, 508C . . . such that an RF voltage of a first phase, $\phi_1$, is applied to odd-numbered (or even-numbered) ones of the rings 508A, 508B, 508C . . . and the same RF voltage of a second phase, $\phi_2$, is applied to even-numbered (or odd-numbered) ones of the rings 508A, 508B, 508C . . . . In some embodiments, $\phi_1$-$\phi_2$ (or $\phi_2$-$\phi_1$=180 degrees such that an opposite phase RF voltage is applied to adjacent ones of the rings 508A, 508B, 508C . . . of the ion carpet 500.

The ring structure 504B of the ion carpet 500 likewise includes a number of axially aligned, electrically conductive, elliptical rings 528A, 528B, 528C . . . formed on the major surface 506A of the circuit board 502 with each successive ring 528A, 528B, 528C . . . reduced in length of both major and minor axes relative to the previous ring. Adjacent rings 528A, 528B, 528C . . . are radially separated from each other by electrically insulating or non-conductive ring areas 530A, 530B, 530C . . . of the planar structure 502. An ion passageway 532, e.g., in the form of a through-hole, having a central axis in common with each of the number of electrically conductive rings 528A, 528B, 528C . . . and electrically insulating or non-conductive areas 530A, 530B, 530C . . . of the planar structure 502 is defined through the planar structure 502. Illustratively, the ring structure 504B is positioned on the major surface 506A of the circuit board 502 such that the ion passageway 532 aligns with the channel 216 or space defined between the opposed circuit boards of an ion steering channel 210, 400 and is also centrally aligned with axially or transversely aligned with sets of pairs of electrically conductive pads formed on the other side (relative to the ion passageway 512), e.g., a right side, of the ion steering channel 210, 400 when the ion carpet 500 is operatively mounted to or operatively positioned adjacent to the ion steering channel 210, 400, e.g., such that the ion passageway 532 bisects or approximately bisects the channel 216 and bisects or approximately bisects the axially or transversely aligned sets of pairs of electrically conductive pads on the side of the ion steering channel opposite that with which the ion passageway 512 is aligned. In the illustrated embodiment the ring structure 504B is identical to the ring structure 504A such that it includes 13 electrically conductive and elliptically shaped rings, although it will be understood that the ring structure 504B may be different from the ring structure 504A by having more or fewer such rings and/or by having rings of other shapes. In embodiments in which the planar member 502 is a circuit board, the electrically conductive rings 508A, 508B, 508C . . . and 528A, 528B, 528C . . . are illustratively applied in a conventional manner on and to the major surface 506A of the circuit board 502 in the form of electrically conductive films or traces, e.g., copper, aluminum and/or other electrically conductive material.

In any case, a conventional AC voltage source 536, e.g., a conventional RF voltage source, is operatively coupled through a capacitor network to each of the electrically conductive rings 528A, 528B, 528C . . . such that an RF voltage of a first phase, $\phi_1$, is applied to odd-numbered (or even-numbered) ones of the rings 528A, 528B, 528C . . . and the same RF voltage of a second phase, $\phi_2$, is applied to even-numbered (or odd-numbered) ones of the rings 528A, 528B, 528C . . . . In some embodiments, $\phi_1$-$\phi_2$ (or $\phi_2$-$\phi_1$)=180 degrees such that an opposite phase RF voltage is applied to adjacent ones of the rings 528A, 528B, 528C . . . of the ion carpet 500.

Generally, the ring structures 504A, 504B of the ion carpet 500 are selectively controllable, together or each independently of the other, to operate as described above with respect to the ion carpet 300 illustrated in FIG. 8. In some embodiments and/or under some operating conditions in which it is desired to focus and pass ions through both ion passageways 512, 532, the ring structures 504A and 504B are controlled via the voltage sources 516 and 532 such that some of the ions travelling toward the major surface 506A of the ion carpet 500 are focused radially inwardly by the RF voltages applied by the voltage source 516 to the ring structure 504A toward and through the central ion passageway 512 and others of the ions travelling toward the major surface 506A of the ion carpet 500 are focused radially inwardly by the RF voltages applied by the voltage source 536 to the ring structure 504B toward and through the central ion passageway 532. In other embodiments and/or under other operating conditions in which it is desired to focus and pass ions only through the ion passageway 512, the ring structure 504A is controlled via the voltage source 516 such that ions travelling toward the major surface 506A of the ion carpet 500 are focused radially inwardly by the RF voltages applied by the voltage source 516 to the ring structure 504A toward and through the central ion passageway 512, and the voltage source 536 is either not activated so that ions traveling toward the major surface 506A of the ion carpet 500 are not radially focused relative to the ring structure 504B and therefore generally do not pass through the central ion passageway 532, or is activated and controlled in a manner that does not cause ions traveling toward the major surface 506A of the ion carpet to be radially focused relative to the ring structure 504B and therefore generally does not provide for the passage of ions through the central ion passageway 532. In still other embodiments and/or under still other operating conditions in which it is desired to focus and pass ions only through the ion passageway 532, the ring structure 504B is controlled via the voltage source 536 such that ions travelling toward the major surface 506A of the ion carpet 500 are focused radially inwardly by the RF voltages applied by the voltage source 536 to the ring structure 504B toward and through the central ion passageway 532, and the voltage source 516 is either not activated so that ions traveling toward the major surface 506A of the ion carpet 500 are not radially focused relative to the ring structure 504A and therefore generally do not pass through the central ion passageway 512, or is activated and controlled in a manner that does not cause ions traveling toward the major surface 506A of the ion carpet to be radially focused relative to the ring structure 504A and therefore generally does not provide for the passage of ions through the central ion passageway 512. Accordingly, the ion carpet 500 may be used in combination with any of the ion gates G1-G4 and/or with any ion steering channel 210, 400 implemented in any of the embodiments 10, 10', 10", 10'" of the hybrid ion mobility spectrometer illustrated in FIGS. 1A-1F.

Figure 12A:
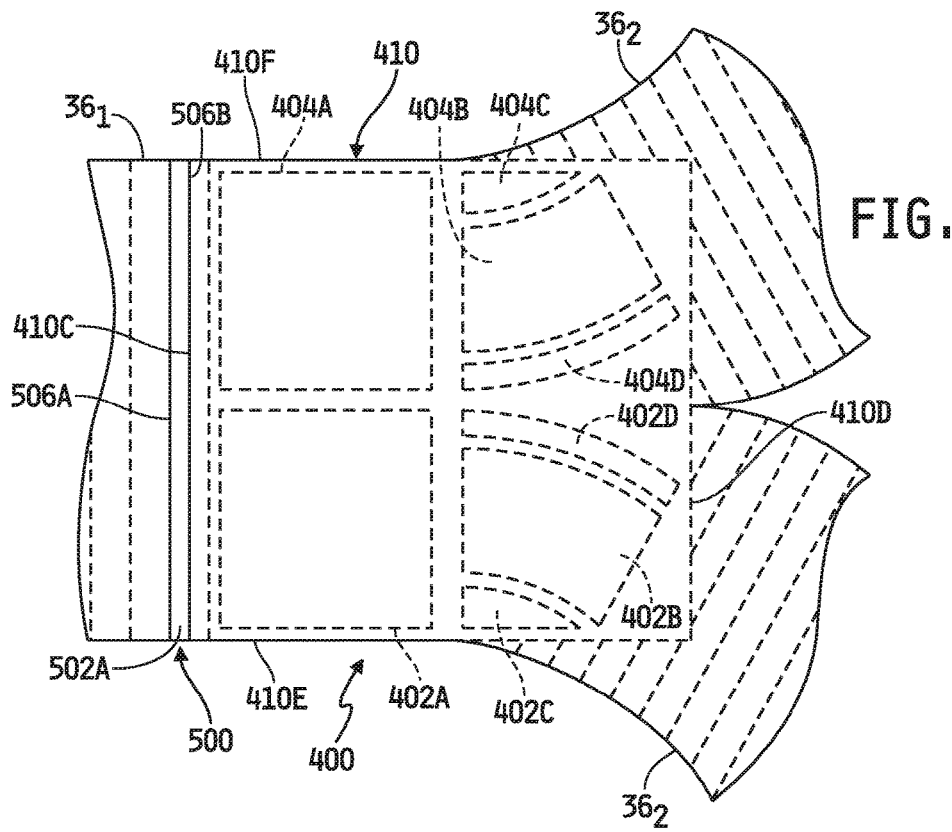
FIG. 12A is a simplified plan diagram illustrating an example combination the ion steering channel partially illustrated in FIG. 9 and the ion carpet illustrated in FIG. 11, illustratively implemented in either of the hybrid ion mobility spectrometers illustrated in FIGS. 1A and 1B.

Referring now to FIG. 12A, an example embodiment is shown of a portion of the hybrid ion mobility spectrometer 10 or 10' in which the ion funnel $32_5$ and the ion gates G1, G2 (FIG. 1A) or G3, G4 (FIG. 1B) positioned in the drift tube section $36_2$ are replaced by an ion carpet 500 coupled to the upstream end of an ion steering channel 400. The ion carpet 500 is illustratively positioned such that the central ion passageway 512 of the ring structure 504A bisects or approximately bisects the space between the planar circuit boards 410 and axially bisects or approximately bisects the electrically conductive pad pairs 404A at the upstream edge 410C of the ion steering channel 400, and that the central ion passageway 532 of the ring structure 504B bisects or approximately bisects the space between the planar circuit boards 410 and axially bisects or approximately bisects the electrically conductive pad pairs 402A at the upstream edge 410C of the ion steering channel 400. Although not shown in FIG. 12A, it will be understood that the voltage sources DC1-DC6 are operatively connected to the electrically conductive pad pairs 402A-402D, 404A-404D as illustrated in FIG. 9 and described above.

When it is desired to direct ions from the drift tube section $36_1$ into the upper arm of the drift tube section $36_2$, the voltage sources 516 and 536 are controlled, as described above, so that ions drifting through the drift tube section $36_1$ toward the major surface 506A of the ion carpet 500 pass through only the ion passageway 512 defined centrally through the ring structure 504A. The voltage sources DC1-DC4 and DC6 are set to VREF and DC5 is set to −XV so as to establish the electric field E2 between the electrically conductive pad pairs 404A and 404B as illustrated in FIG. 10B. Thus as ions drift through the drift tube section $36_1$ toward the major surface 506A of the ion carpet 500, such ions are radially focused by the ring structure 504A and pass through the ion passageway 512 thereof where such ions are then steered or guided by the electric field E2 toward and into the upper arm of the drift tube section $36_2$.

When it is desired to direct ions from the drift tube section $36_1$ into the lower arm of the drift tube section $36_2$, the voltage sources 516 and 536 are controlled, as described above, so that ions drifting through the drift tube section $36_1$ toward the major surface 506A of the ion carpet 500 pass through only the ion passageway 532 defined centrally through the ring structure 504B. The voltage sources DC1, DC2 and DC4-DC6 are set to VREF and DC3 is set to −XV so as to establish the electric field E1 between the electrically conductive pad pairs 402A and 402B as illustrated in FIG. 10A. Thus as ions drift through the drift tube section $36_1$ toward the major surface 506A of the ion carpet 500, such ions are radially focused by the ring structure 504B and pass through the ion passageway 532 where such ions are then steered or guided by the electric field E1 toward and into the lower arm of the drift tube section $36_2$.

Figure 12B:
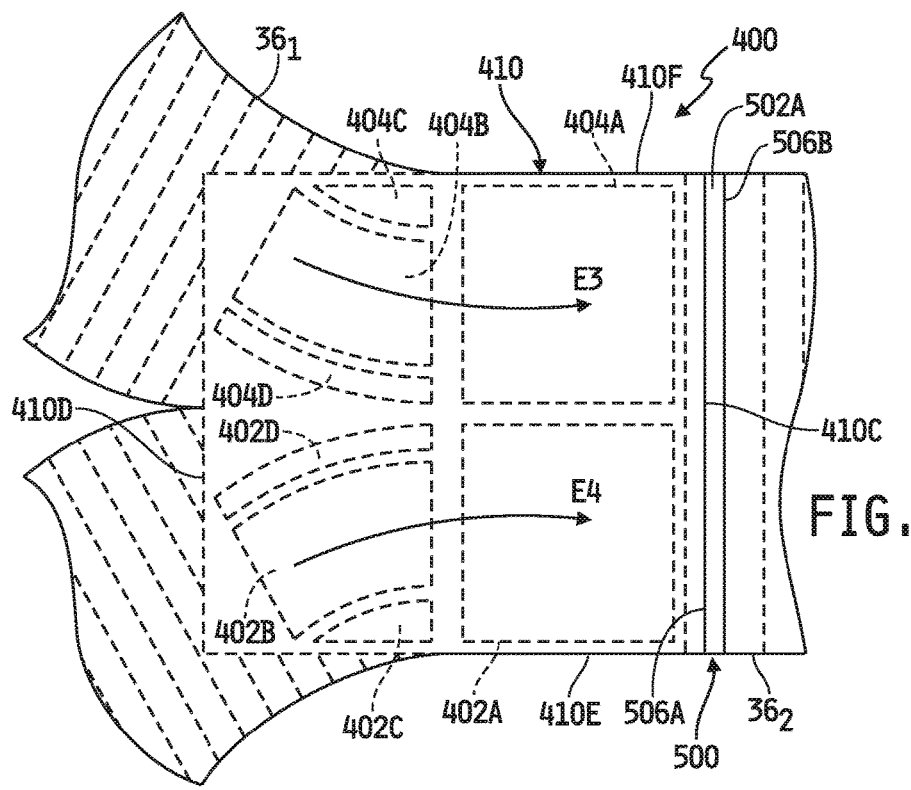
FIG. 12B is a simplified plan diagram illustrating another example combination the ion steering channel partially illustrated in FIG. 9 and the ion carpet illustrated in FIG. 11, illustratively implemented in the hybrid ion mobility spectrometer illustrated in FIG. 1A.

Referring now to FIG. 12B, an example embodiment is shown of a portion of the hybrid ion mobility spectrometer 10 in which the ion funnel $32_5$ and the ion gate G3 positioned in the drift tube section $36_1$ are replaced by an ion carpet 500 coupled to the downstream end of an ion steering channel 400 rotated 180 degrees relative to the configuration illustrated in FIGS. 9-10A. The ion carpet 500 is illustratively positioned such that the central ion passageway 512 of the ring structure 504A bisects or approximately bisects the space between the planar circuit boards 410 and axially bisects or approximately bisects the electrically conductive pad pairs 404A at the (now) downstream edge 410C of the ion steering channel 400, and that the central ion passageway 532 of the ring structure 504B bisects or approximately bisects the space between the planar circuit boards 410 and axially bisects or approximately bisects the electrically conductive pad pairs 402A at the (now) downstream edge 410C of the ion steering channel 400. Although not shown in FIG. 12B, it will be understood that the voltage sources DC1-DC6 are operatively connected to the electrically conductive pad pairs 402A-402D, 404A-404D as illustrated in FIG. 9 and described above.

When it is desired to direct ions from the upper arm of the drift tube section $36_1$ into the drift tube section $36_2$, the voltage sources DC1 and DC3-DC6 are set to VREF and DC2 is set to −XV so as to establish an electric field E3 between the electrically conductive pad pairs 404B, 404C, 404D and 404B in the direction of the ion carpet 500. The voltage sources 516 and 536 are controlled, as described above, so that ions being steered or guided by the electric field E3 toward the major surface 506A of the ion carpet 500 are radially focused by the ring structure 504A and pass through only the ion passageway 512 defined centrally through the ring structure 504A. Thus as ions drift through and along the upper arm of the drift tube section $36_1$ toward the ion steering channel 400, such ions are steered or guided by the electric field E3 toward the ring structure 504A defined on the major surface 506A of the ion carpet 500, and such ions are then radially focused by the ring structure 504A and pass through the ion passageway 512 thereof and into the drift tube section $36_2$.

When it is desired to direct ions from the lower arm of the drift tube section $36_1$ into the drift tube section $36_2$, the voltage sources DC2-DC6 are set to VREF and DC1 is set to −XV so as to establish an electric field E4 between the electrically conductive pad pairs 402B, 402C, 402D and 402B in the direction of the ion carpet 500. The voltage sources 516 and 536 are controlled, as described above, so that ions being steered or guided by the electric field E4 toward the major surface 506A of the ion carpet 500 are radially focused by the ring structure 504B and pass through only the ion passageway 532 defined centrally through the ring structure 504B. Thus as ions drift through and along the lower arm of the drift tube section $36_1$ toward the ion steering channel 400, such ions are steered or guided by the electric field E4 toward the ring structure 504B defined on the major surface 506A of the ion carpet 500, and such ions are then radially focused by the ring structure 504B and pass through the ion passageway 532 thereof and into the drift tube section $36_2$.

In some alternate embodiments of the structure illustrated in FIG. 12B, the ion carpet 500 may be replaced by an ion carpet 300 positioned in the upper arm of the drift tube section $36_1$ and spaced apart from or positioned adjacent to the ion entrance end of the electrically conductive pad pairs 404B, and another ion carpet 300 positioned in the lower arm of the drift tube section $36_1$ and spaced apart from or positioned adjacent to the ion entrance end of the electrically conductive pad pairs 402B. Such ion carpets 300 may illustratively be controlled similarly as just described with respect to the ion carpet 500 to selectively guide ions from the upper or lower arms of the drift tube section $36_1$ into the drift tube section $36_2$.

In other alternate embodiments of the hybrid ion mobility spectrometer 10 illustrated in FIG. 1A, some the structures illustrated in FIGS. 12A and 12B may be combined to replace the ion funnel $32_5$ and the ion gates G1-G3. In one example, the ion steering channels 400 illustrated in FIGS. 12A and 12B may be positioned adjacent to each other with an ion carpet 500 positioned therebetween. In another example, the ion steering channels 400 illustrated in FIGS. 12A and 12B may be positioned adjacent to each other, e.g., in cascaded relationship, and individual ion carpets 300 may be positioned in the upper and lower arms of the drift tube segment $36_1$ and/or in the upper and lower arms of the drift tube segment $36_2$. Those skilled in the art will recognize other combinations of one or more ion steering channels 400 and one or more ion carpets 300 and/or one or more ion carpets 500 that may replace one or more corresponding ion funnels, ion gates and/or ion gate combinations in any of the hybrid ion mobility spectrometer embodiments 10, 10', 10", 10'" described herein and/or in any other conventional ion separation instrument, and it will be understood that this disclosure contemplates any such other combinations.

Figure 13:
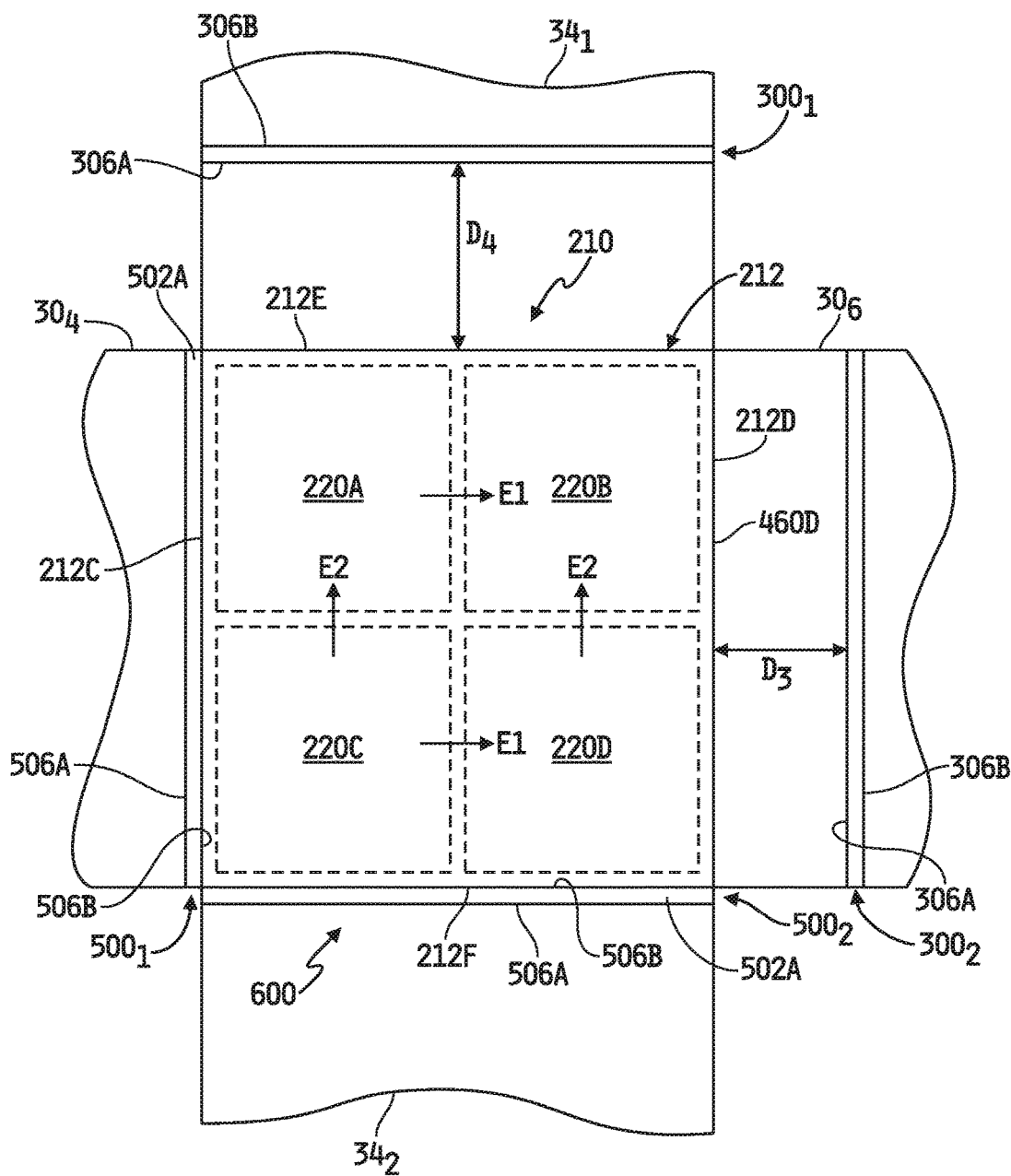
FIG. 13 is a simplified plan diagram illustrating an example combination the ion steering channel illustrated in FIG. 6, two of the ion carpets illustrated in FIG. 8 and two of the ion carpets illustrated in FIG. 11, illustratively implemented in the hybrid ion mobility spectrometer illustrated in FIGS. 1D and 1E.

Referring now to FIG. 13, an example embodiment is shown of a portion of the hybrid ion mobility spectrometer 10'" in which the ion transition region 80 is replaced by an ion transition region 600 including a combination of an ion steering channel 210, two ion carpets $500_1$, $500_2$ and two ion carpets $300_1$, $300_2$. The ion steering channel 210 is illustratively arranged as illustrated in FIG. 6 and with the upstream edges 212C, 214C of the circuit boards 212, 214 at or adjacent the ion outlet end of the drift tube section $30_4$, with the downstream edges 212D, 214D at or adjacent to the ion inlet end of the drift tube section $30_6$, with the side edges 212E, 214E at or adjacent to the ion inlet end of the drift tube section $34_1$ and with the side edges 212F, 214F at or adjacent to the ion outlet end of the drift tube section $34_2$ (only the edges 212C, 212D, 212E, 212F of the circuit board 212 depicted in the top plan view illustrated in FIG. 13). An ion carpet $500_1$ is illustratively positioned at or adjacent to the upstream edges 212C, 214C of the ion steering channel 210 such that the major surface 506A thereof having the ring structures 504A, 504B formed thereon faces away from the ion steering channel 210, and another ion carpet $500_2$ is illustratively positioned at or adjacent to the side edges 212F, 214F of the ion steering channel 210 such that the major surface 506A thereof having the ring structures 504A, 504B formed therein faces away from the ion steering channel 210. An ion carpet $300_1$ is illustratively positioned in the drift tube section $30_6$ with the major surface 306A thereof having the ring structure 304 formed thereon facing the ion steering channel 210 and illustratively spaced apart from the downstream edges 212D, 214D by a distance D3, and another ion carpet $300_2$ is illustratively positioned in the drift tube section $34_1$ with the major surface 306A thereof having the ring structure 304 formed thereon facing the ion steering channel 210 and illustratively spaced apart from the side edges 212E, 214E by a distance D4. The ion carpets $300_1$, $300_2$ are each illustratively positioned such that the central passageway 312 of the ring structure 304 bisects or approximately bisects the channel 216 of the ion steering channel 210 and centrally bisects or approximately bisects the circuit boards 212, 214. The ion carpets $500_1$, $500_2$ are illustratively positioned such that the central ion passageways 512, 532 of the ring structures 504A, 504B respectively bisect or approximately bisect the channel 216 of the ion steering channel 210. The ion carpet $500_1$ is further illustratively positioned such that the central ion passageway 512 of the ring structure 504A bisects or approximately bisects the aligned electrically conductive pad pairs 220A, 220A' and 220B, 200B' at the upstream edge 212C, 214C of the ion steering channel 210, and that the central ion passageway 532 of the ring structure 504B bisects or approximately bisects the aligned electrically conductive pad pairs 220C, 220C' and 220D, 200D' at the upstream edge 212C, 214C of the ion steering channel 210 (only the electrically conductive pads 220A-220D of the circuit board 212 are depicted in dashed-line in the top plan view illustrated in FIG. 13). The ion carpet $500_2$ is further illustratively positioned such that the central ion passageway 512 of the ring structure 504A bisects or approximately bisects the aligned electrically conductive pad pairs 220C, 220C' and 220A, 200A' at the side edge 212F, 214F of the ion steering channel 210, and that the central ion passageway 532 of the ring structure 504B bisects or approximately bisects the aligned electrically conductive pad pairs 220D, 220D' and 220B, 200B' at the side edge 212E, 214E of the ion steering channel 210. Although not shown in FIG. 13, it will be understood that the voltage sources DC1-DC4 are operatively connected to the electrically conductive pad pairs 220A/220A', 220B/220B', 220C/220C' and 220D/220D' as illustrated in FIG. 6 and described above.

When it is desired to axially pass ions from the drift tube section $30_4$ into the drift tube section $30_6$, the voltage sources DC1 and DC2 are set to VREF and the voltage sources DC3 and DC4 are set to −XV so as to establish the electric field E1 between the aligned electrically conductive pad pairs 220A, 220A' and 220B, 220B' and between the aligned electrically conductive pad pairs 220C, 220C' and 220D, 220D' in the axial direction of the drift tube sections $30_4$ and $30_6$. The voltage sources 516 and 536 for the ion carpet $500_1$ are controlled, as described above, so that ions drifting through the drift tube section $30_1$ toward the major surface 506A of the ion carpet $500_1$ are radially focused by both ring structures 504A and 504B and therefore pass through both of the ion passageways 512, 532 defined centrally through the ring structures 504A, 504B respectively. Thus as ions drift through and along the drift tube section $30_4$, such ions are radially focused by the ring structures 504A, 504B of the ion carpet $500_1$ and pass in separate focused ion streams through the ion passageways 512, 532 respectively whereupon the focused ion stream exiting the ion passageway 512 is steered or guided by the electric field E1 established between the electrically conductive pad pairs 220A, 220A' and 220B, 220B' into the drift tube section $30_6$ and the focused ion stream exiting the ion passageway 532 is likewise steered or guided by the electric field E1 established between the electrically conductive pad pairs 220C, 220C' and 220D, 220D' into the drift tube section $30_6$. As the two separate focused ion streams drift through the distance D3 of the drift tube section $30_6$ and toward the ion carpet $300_2$, they are radially focused by the ring structure 304 of the ion carpet $300_2$ into a single, combined ion stream to pass through the ion passageway 312 of the ion carpet $300_2$ which ion passageway 312 is illustratively axially aligned with the ion travel axis 72 of the single-pass drift tube 12''' illustrated in FIG. 1E and described above. Illustratively, the distance D3 is selected so allow the two separate focused ion streams exiting the ion steering channel 210 to be combined and radially focused into a single focused ion stream to pass through the passageway 312 of the ion carpet $300_2$.

When it is desired to transversely pass ions from the drift tube section $30_4$ of the single-pass drift tube 12''' into the drift tube section $34_1$ of the multiple-pass drift tube 14'' illustrated in FIGS. 1D and 1E, the voltage sources DC2 and DC4 are set to VREF and the voltage sources DC1 and DC3 are set to −XV so as to establish the electric field E2 between the aligned electrically conductive pad pairs 220C, 220C' and 220A, 220A' and between the aligned electrically conductive pad pairs 220D, 220D' and 220B, 220B' in the axial direction of the drift tube sections $34_1$ and $34_2$. The voltage sources 516 and 536 for the ion carpet $500_1$ are controlled, as described above, so that ions drifting through the drift tube section $30_1$ toward the major surface 506A of the ion carpet $500_1$ are radially focused only by the ring structure 504B and therefore pass only through the ion passageways 532 defined centrally through the ring structure 504B. As ions drift through and along the drift tube section $30_4$ and are radially focused only by the ring structure 504B of the ion carpet $500_1$, such ions pass in a single focused ion stream through the ion passageway 532 in a direction generally parallel with the ion travel axis 72 of the single-pass drift tube 12''' toward the aligned electrically conductive pads 220C, 220C' and 220D, 220D'. As the focused ion stream exits the ion passageway 532, however, it is steered or guided by the electric field E2 established between the electrically conductive pad pairs 220C, 220C' and 220A, 220A' and between the electrically conductive pad pairs 220D, 220D' and 220B, 220B' to change directions by approximately 90 degrees so as to pass into the drift tube section $34_1$ of the multiple-pass drift tube 14''. As the redirected ions drift through the distance D4 of the drift tube section $34_1$ and toward the ion carpet $300_1$, they are radially focused by the ring structure 304 of the ion carpet $300_1$ so as to pass through the ion passageway 312 of the ion carpet $300_1$ which ion passageway 312 is illustratively axially aligned with the ion travel axis 70 of the multiple-pass drift tube 14'' illustrated in FIGS. 1E and 1F and described above.

Illustratively, the distance D4 is selected so allow the two separate focused ion streams exiting the ion steering channel 210 to be combined and radially focused into a single focused ion stream to pass through the passageway 312 of the ion carpet $300_1$.

As described above, the multiple-pass drift tube 14'' is illustratively controlled to allow ions to travel therethrough any number of times, and in so doing the voltage sources DC1 and DC2 are the voltage sources DC2 and DC4 are maintained at VREF and the voltage sources DC1 and DC3 are maintained at −XV so as to maintain the electric field E2 between the aligned electrically conductive pad pairs 220C, 220C' and 220A, 220A' and between the aligned electrically conductive pad pairs 220D, 220D' and 220B, 220B' in the axial direction of the drift tube sections $34_1$ and $34_2$. The voltage sources 516 and 536 for the ion carpet $500_2$ are controlled, as described above, so that ions drifting through the drift tube section $34_2$ toward the major surface 506A of the ion carpet $500_2$ are radially focused by both ring structures 504A and 504B and therefore pass through both of the ion passageways 512, 532 defined centrally through the ring structures 504A, 504B respectively. Thus as ions drift through and along the drift tube section $34_2$, such ions are radially focused by the ring structures 504A, 504B of the ion carpet $500_2$ and pass in separate focused ion streams through the ion passageways 512, 532 respectively whereupon the focused ion stream exiting the ion passageway 512 is steered or guided by the electric field E2 established between the electrically conductive pad pairs 220C, 220C' and 220A, 220A' into the drift tube section $34_1$ and the focused ion stream exiting the ion passageway 532 is likewise steered or guided by the electric field E2 established between the electrically conductive pad pairs 220D, 220D' and 220E, 220E' into the drift tube section $34_1$. As the two separate focused ion streams drift through the distance D4 of the drift tube section $34_1$ and toward the ion carpet $300_1$, they are radially focused by the ring structure 304 of the ion carpet $300_1$ into a single, combined ion stream to pass through the ion passageway 312 of the ion carpet $300_1$ which passageway 312 is illustratively axially aligned with the ion travel axis 70 of the multiple-pass drift tube 14'' illustrated in FIG. 1D and described above.

When it is desired to transversely pass ions from the drift tube section $34_2$ of the multiple-pass drift tube 14'' into the drift tube section $30_6$ of the single-pass drift tube 12''' illustrated in FIGS. 1D and 1E, e.g., after ions have circulated about the multiple-pass drift tube 14' a desired number of times, the voltage sources DC1 and DC2 are set to VREF and the voltage sources DC3 and DC4 are set to −XV so as to reestablish the electric field E1 between the aligned electrically conductive pad pairs 220A, 220A' and 220B, 220B' and between the aligned electrically conductive pad pairs 220C, 220C' and 220D, 220D' in the axial direction of the drift tube sections $30_4$ and $30_6$. The voltage sources 516 and 536 for the ion carpet $500_2$ are illustratively controlled, as described above, so that ions drifting through the drift tube section $34_2$ toward the major surface 506A of the ion carpet $500_2$ are radially focused only by the ring structure 504A and therefore pass only through the ion passageway 516 defined centrally through the ring structure 504A. As ions drift through and along the drift tube section $34_2$ and are radially focused only by the ring structure 504A of the ion carpet $500_2$, such ions pass in a single focused ion stream through the ion passageway 512 in a direction generally parallel with the ion travel axis 70 of the multiple-pass drift tube 14'' toward the aligned electrically conductive pads 220C, 220C' and 220A, 220A'. As the focused ion stream exits the ion passageway 512, however, it is steered or guided by the electric field E1 established between the electrically conductive pad pairs 220C, 220C' and 220D, 220D' and between the electrically conductive pad pairs 220A, 220A' and 220B, 220B' to change directions by approximately 90 degrees so as to pass into the drift tube section $30_6$ of the single-pass drift tube 12'''. As the redirected ions drift through the distance D3 of the drift tube section $30_6$ and toward the ion carpet $300_2$, they are radially focused by the ring structure 304 of the ion carpet $300_2$ so as to pass through the ion passageway 312 of the ion carpet $300_2$ which ion passageway 312 is, as described above, axially aligned with the ion travel axis 72 of the single-pass drift tube 12'''.

It will be understood that the embodiment illustrated in FIG. 13 represents only one non-limiting combination of the ion steering channel 210 and the ion carpets 300 and 500 implemented in the hybrid ion mobility spectrometer illustrated in FIGS. 1D and 1E, and that that other combinations which may include more or fewer ion carpets 300 and/or 500, which may include additional ion steering channels 210 and/or which may include one or more of ion steering channels 400 are contemplated by this disclosure. As one specific and non-limiting example, the embodiment 600 illustrated in FIG. 13 may alternatively include one or more ion carpets 300 in place of either or both of the ion carpets 500. As another non-limiting example, one or more of the ion carpets 300, 500 may be omitted in favor one or more of the ion funnels illustrated in FIGS. 1D and 1E. Those skilled in the art will recognize other combinations of one or more ion steering channels 212 and one or more ion carpets 300 and/or one or more ion carpets 500 that may replace one or more corresponding ion funnels, ion gates and/or ion gate combinations in any of the hybrid ion mobility spectrometer embodiments 10, 10', 10", 10''' described herein and/or in any other conventional ion separation instrument, and it will be understood that this disclosure contemplates any such other combinations.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, in some alternate embodiments, one or more conventional ion analytical instruments may be substituted for either or both of the ion source 18 and the ion detector 22 such that alternate and/or additional ion separation, ion conformation alteration, ion processing and/or ion analysis may be carried out on ions prior to entering and/or after exiting the single-pass drift tube 12, 12', 12", 12'''. Alternatively or additionally, one or more conventional ion analytical instruments may be positioned within or interposed along either or both of the single-pass drift tube 12, 12', 12", 12''' and the multiple-pass drift tube 14, 14', 14" such that alternate and/or additional ion separation, ion conformation alteration, ion processing and/or ion analysis may be carried out within or along the single-pass drift tube 12, 12', 12", 12''' and/or the multiple-pass drift tube 14, 14', 14". In any case, examples of such conventional ion analytical instruments that precede the ion inlet 16 of the single-pass drift tube 12, 12', 12", 12''', that follow the ion outlet 20 of the single-pass drift tube 12, 12', 12", 12''' and/or that are positioned within or interposed along the single-pass drift tube 12, 12', 12", 12''' and/or the multiple-pass drift tube 14, 14', 14" may include, but are not limited to, one or more drift tubes identical to or different from the single-pass drift tube 12, 12', 12", 12''' and/or the multiple-pass drift tube 14, 14', 14", one or more mass analyzers and/or mass spectrometers, one or more liquid and/or gas chromatographs, one or mass filters (e.g., one or more multiple-pole mass filters), one or more collision cells and/or other ion fragmentation devices or regions, one or more ion activation regions in which an electric field is established that is high enough to alter the conformation of one or more ions but not high enough to fragment ions, or the like. It will be further understood that in embodiments that include two or more such conventional ion analytical instruments together, such two or more conventional ion analytical instruments may be positioned in parallel relative to each other, in series relative to each other (i.e., cascaded) or any combination of series and parallel.

Additionally or alternatively, those skilled in the art will recognize that the multiple-pass drift tube 14 illustrated in any of FIGS. 1A-1B can, in some embodiments, be provided in the form of two or more series-connected and/or parallel-connected multiple-pass drift tubes. Alternatively or additionally still, such one or more multiple-pass drift tubes 14 can be augmented by one or more single-pass drift tubes 12 and/or by one or more conventional analytical instruments of the type described by example in the previous paragraph.

As another example, it will be understood that while the various embodiments of the hybrid ion mobility spectrometer 10, 10', 10", 10''' illustrated and described herein include a multiple-pass drift tube 14, 14', 14" coupled to a single-pass drift tube 12, 12', 12", 12''' between an ion inlet 16 and an ion outlet 20 of the single-pass drift tube 12, 12', 12", 12''', this disclosure contemplates alternative embodiments in which the multiple-pass drift tube 14, 14', 14" or other suitable multiple-pass drift tube is positioned upstream of the single-pass drift tube 12, 12', 12", 12''', i.e., prior to the ion inlet 16 and/or downstream of the single-pass drift tube 12, 12', 12", 12''', i.e., following the ion outlet 20.

As still another example, operation of the ion gates G1-G3 or G1-G4 has been described herein in which such ion gates G1-G3 or G1-G4 are controlled to block or allow passage therethrough of some or all ions from a preceding, e.g. upstream, stage or section of the hybrid ion mobility spectrometer 10, 10', 10", 10'''. It will be understood that this disclosure contemplates embodiments in which any one or more of the gates G1-G3 or G1-G4 may be controlled to intermediate positions, i.e., between their open and closed positions, to allow pass therethrough of only a fraction of the ions at any one or more times. This would allow, for example, operation of the single-pass drift tube 12, 12', 12", 12''' to be carried out simultaneously with the operation of the multiple-pass drift tube 14, 14', 14" such that ions exiting more quickly from the single-pass drift tube 12, 12', 12", 12''' can be analyzed prior to analyzing ions exiting the multiple-pass drift tube.

What is claimed is:

1. A hybrid ion mobility spectrometer, comprising:
   a single-pass drift tube having an ion inlet at one end and an ion outlet at an opposite end, the single-pass drift tube configured to separate in time ions entering the ion inlet thereof and traveling therethrough according to a first function of ion mobility,
   a multiple-pass drift tube having an ion inlet and an ion outlet each coupled to the single pass drift tube between the ion inlet of the single-pass drift tube and the ion outlet of the single-pass drift tube, the multiple-pass drift tube configured to separate in time ions entering the ion inlet of the multiple-pass drift tube and traveling one or more times therethrough according to the first or a second function of ion mobility, and at least one ion steering channel controllable to selectively pass ions traveling through the single-pass drift tube into the multiple-pass drift tube via the ion inlet of the multiple-pass drift tube and to selectively pass ions traveling through the multiple-pass drift tube into the single-pass drift tube via the ion outlet of the multiple-pass drift tube.

2. The hybrid ion mobility spectrometer of claim 1, wherein the at least one ion steering channel is selectively controllable to a first operating condition in which the at least one ion steering channel directs ions traveling through the single-pass drift tube to continue traveling through the single-pass drift tube to the ion outlet thereof, and to a second operating condition different from the first operating condition in which the at least one ion steering channel passes ions traveling through the single-pass drift tube into the multiple-pass drift tube, and further comprising a plurality of voltage sources to produce the different first and second ion steering channel operating conditions.

3. The hybrid ion mobility spectrometer of claim 2, wherein the at least one ion steering channel is selectively controllable to a third operating condition in which the at least one ion steering channel directs ions traveling through the multiple-pass drift tube to continue traveling through the multiple-pass drift tube, and to a fourth operating condition different from the third operating condition in which the at least one ion steering channel passes ions traveling through the multiple-pass drift tube into the single-pass drift tube such that the ions passed into the single-pass drift tube travel to the ion outlet thereof, And wherein the plurality of voltage sources is configured produce the different third and fourth ion steering channel operating conditions.

4. The hybrid ion mobility spectrometer of claim 1, wherein the at least one ion steering channel comprises:

a first electrically insulating planar member having a major surface on which is formed a plurality of electrically conductive pads, and a second electrically insulating planar member having a major surface on which is formed a plurality of electrically conductive pads, the major surface of the first electrically insulating planar member facing, and spaced apart from, the major surface of the second electrically insulating planar member to form an ion directing channel therebetween with each of the plurality of electrically conductive pads formed on the major surface of the first electrically insulating planar member juxtaposed with a different one of the plurality of electrically conductive pads formed on the major surface of the second electrically insulating planar member to form a plurality of opposed electrically conductive pad pairs within the ion directing channel, the ion directing channel open to the single-pass drift tube and to the multiple-pass drift tube, a first plurality of voltage sources each electrically connected to a different one or a combination of the plurality of opposed electrically conductive pad pairs, the first plurality of voltage sources selectively controllable to a first set of potentials to establish at least a first electric field within the ion directing channel in a direction that causes ions traveling therein from the single-pass drift tube to pass into the multiple-pass drift tube via the ion inlet thereof, the first plurality of voltage sources selectively controllable to a second set of potentials to establish at least a second electric field within the ion directing channel in a direction that causes ions traveling therein from the ion outlet of the multiple-pass drift tube to pass into the single-pass drift tube downstream of the ion directing channel.

5. The hybrid ion mobility spectrometer of claim 4, wherein one or more voltage sources within the first plurality of voltage sources is programmable to control timing of production of the first and second sets of potentials.

6. The hybrid ion mobility spectrometer of claim 4, further comprising a processor electrically coupled to at least one of the first plurality of voltage sources, the processor to control timing of production of at least one of the first and second sets of potentials.

7. The hybrid ion mobility spectrometer claim 4, further comprising a second plurality of voltage sources to produce first and second sets of voltage signals, wherein the single-pass drift tube is responsive to the first set of voltage signals to separate ions in time according to the first function of ion mobility and the multiple-pass drift tube is responsive to the second set of voltage signals to separate ions in time according to the first or second function of ion mobility.

8. The hybrid ion mobility spectrometer of claim 7, further comprising a processor electrically coupled to at least one of the second plurality of voltage sources, the processor to control production of at least one of the first and second sets of voltage signals.

9. The hybrid ion mobility spectrometer of claim 1, wherein the multiple-pass drift tube comprises a closed-path drift tube, the ion inlet of the multiple-pass drift tube comprises an ion inlet tube having an ion outlet integrally formed with the multiple-pass drift tube and the ion outlet of the multiple-pass drift tube comprises an ion outlet tube having an ion inlet integrally formed with the multiple-pass drift tube.

10. The hybrid ion mobility spectrometer of claim 9, wherein the at least one ion steering channel comprises:

a first ion steering channel disposed in or coupled to the multiple-pass drift tube and controllable to selectively pass ions traveling through the single-pass drift tube into the multiple-pass drift tube via the ion inlet of the multiple-pass drift tube, and a second ion steering channel disposed in or coupled to the multiple-pass drift tube and controllable to selectively pass ions traveling through the multiple-pass drift tube into the single-pass drift tube via the ion outlet of the multiple-pass drift tube.

11. The hybrid ion mobility spectrometer of claim 10, further comprising:

at least one ion carpet positioned in at least one of the single-pass drift tube and the multiple-pass drift tube, the at least one ion carpet including a planar member defining a major surface facing opposite to a direction of ion travel through the at least one of the single-pass drift tube and the multiple-pass drift tube, the major surface of the planar member having a plurality of electrically conductive rings formed thereon each axially aligned with an ion passageway defined through the planar member, each successively smaller than an adjacent ring surrounding an outer periphery thereof and each axially spaced apart from rings adjacent thereto, and at least one AC voltage source producing first and second AC voltage signals each opposite in phase to the other, the first and second AC voltage signals alternatingly coupled to the plurality of electrically conductive rings such that each ring is opposite in phase to adjacent rings to focus ions traveling toward the major surface radially inwardly such that the radially focused ions travel through the ion passageway.

12. The hybrid ion mobility spectrometer of claim 1, wherein the single-pass drift tube comprises a first plurality of linearly arranged, cascaded drift tube segments,
   wherein the multiple-pass drift tube is a closed-path drift tube and comprises a second plurality of cascaded drift tube segments with an ion outlet of a last one of the second plurality of cascaded drift tube segments coupled to an ion inlet of a first one of the second plurality of cascaded drift tube segments,
   and wherein the ion inlet of the multiple-pass drift tube is coupled to one of the first plurality of drift tube segments and the ion outlet of the multiple-pass drift tube is coupled to another of the first plurality of drift tube segments downstream of the one of the first plurality of drift tube segments.

13. The hybrid ion mobility spectrometer of claim 1, wherein the single-pass drift tube comprises a first plurality of linearly arranged, cascaded drift tube segments, defining a first direction of ion travel axially therethrough,
   and wherein the multiple-pass drift tube comprises a second plurality of cascaded drift tube segments defining a second direction of ion travel axially therethrough, the second direction of ion travel different from the first direction of ion travel, an ion inlet of a first one of the second plurality of cascaded drift tube segments defining the ion inlet of the multiple-pass drift tube and an ion outlet of a last one of the second plurality of cascaded drift tube segments defining the ion outlet of the multiple-pass drift tube,
   and wherein the hybrid ion mobility spectrometer further comprises an ion transition region interposed at opposite ends thereof between two adjacent ones of the first plurality of cascaded drift tube segments, the ion transition region coupled on one side thereof to the ion inlet of the multiple-pass drift tube and coupled on an opposite side thereof to the ion outlet of the multiple-pass drift tube such that the ion transition region and the multiple-pass drift tube together define a closed-path drift tube,
   and wherein the at least one ion steering channel comprises an ion steering channel disposed within the ion transition region and defining both the first and second directions of ion travel therethrough, the ion steering channel controllable to selectively pass ions traveling therein from the single-pass drift tube into the ion inlet of the multiple-pass drift tube and to selectively pass ions traveling therein from the ion outlet of the multiple-pass drift tube into the single-pass drift tube downstream of the ion transition region.

14. The hybrid ion mobility spectrometer of claim 13, wherein the ion steering channel comprises:
   a first electrically insulating planar member having a major surface on which is formed a plurality of electrically conductive pads,
   a second electrically insulating planar member having a major surface on which is formed a plurality of electrically conductive pads, the major surface of the first electrically insulating planar member facing, and spaced apart from, the major surface of the second electrically insulating planar member to form an ion directing channel therebetween with each of the plurality of electrically conductive pads formed on the major surface of the first electrically insulating planar member juxtaposed with a different one of the plurality of electrically conductive pads formed on the major surface of the second electrically insulating planar member to form a plurality of opposed electrically conductive pad pairs within the ion directing channel, the ion directing channel defining both the first and second directions of ion travel therethrough, and
   a plurality of voltage sources each electrically connected to a different one or a combination of the plurality of opposed electrically conductive pad pairs, the plurality of voltage sources selectively controllable to a first set of potentials to establish at least a first electric field within the ion directing channel in a direction that causes ions traveling therein from the single-pass drift tube to pass into the multiple-pass drift tube via the ion inlet thereof, the first plurality of voltage sources selectively controllable to a second set of potentials to establish at least a second electric field within the ion directing channel in a direction that causes ions traveling therein from the multiple-pass drift tube to pass into the single-pass drift tube downstream of the ion transition region.

15. A hybrid ion mobility spectrometer, comprising:
   a single-pass drift tube configured to separate in time ions traveling axially therethrough in a first direction of ion travel according to a first function of ion mobility,
   a closed-path, multiple-pass drift tube configured to separate in time ions traveling axially therethrough one or more times in a second direction of ion travel according to the first or a second function of ion mobility, the second direction of ion travel different from the first direction of ion travel, and
   an ion steering channel disposed in-line with the single-pass drift tube and in-line with the multiple-pass drift tube, the ion steering channel selectively controllable to steer ions traveling therein from the single-pass drift tube into the multiple-pass drift tube, the ion steering channel further selectively controllable to steer ions traveling therein from the multiple-pass drift tube into the single-pass drift tube.

16. The hybrid ion mobility spectrometer of claim 15, wherein the ion steering channel is further selectively controllable to allow ions traveling therein from the single-pass drift tube to pass into the single-pass drift tube downstream of the ion steering channel,
   and wherein the ion steering channel is further selectively controllable to pass ions traveling therein from the multiple pass drift tube back into the multiple-pass drift tube.

17. The hybrid ion mobility spectrometer of claim 15, wherein the ion steering channel comprises:
   a first electrically insulating planar member having a major surface on which is formed a plurality of electrically conductive pads,
   a second electrically insulating planar member having a major surface on which is formed a plurality of electrically conductive pads, the major surface of the first electrically insulating planar member facing, and spaced apart from, the major surface of the second electrically insulating planar member to form an ion directing channel therebetween with each of the plurality of electrically conductive pads formed on the major surface of the first electrically insulating planar member juxtaposed with a different one of the plurality of electrically conductive pads formed on the major surface of the second electrically insulating planar member to form a plurality of opposed electrically conductive pad pairs within the ion directing channel, and a plurality of voltage sources each electrically connected to a different one or a combination of the plurality of opposed electrically conductive pad pairs, the plurality of voltage sources selectively controllable to a first set of potentials to establish at least a first electric field within the ion directing channel in a direction that steers ions traveling therein from the single-pass drift tube into the multiple-pass drift tube, the first plurality of voltage sources selectively controllable to a second set of potentials to establish at least a second electric field within the ion directing channel in a direction that steers ions traveling therein from the multiple-pass drift tube into the single-pass drift tube downstream of the ion steering channel.

18. The hybrid ion mobility spectrometer of claim 17, wherein the first electric field established within the ion directing channel also causes ions traveling therein from the multiple-pass drift tube to pass back into the multiple-pass drift tube, and wherein the second electric field established within the ion directing channel also causes ions traveling therein from the single-pass drift tube to pass into the single-pass drift tube downstream of the ion directing channel.

19. The hybrid ion mobility spectrometer of claim 15, further comprising:

at least one ion carpet positioned in at least one of the single-pass drift tube and the multiple-pass drift tube, the at least one ion carpet including a planar member defining a major surface facing opposite to a direction of ion travel through the at least one of the single-pass drift tube and the multiple-pass drift tube, the major surface of the planar member having a plurality of electrically conductive rings formed thereon each axially aligned with an ion passageway defined through the planar member, each successively smaller than an adjacent ring surrounding an outer periphery thereof and each axially spaced apart from rings adjacent thereto, and at least one AC voltage source producing first and second AC voltage signals each opposite in phase to the other, the first and second AC voltage signals alternatingly coupled to the plurality of electrically conductive rings such that each ring is opposite in phase to adjacent rings to focus ions traveling toward the major surface radially inwardly such that the radially focused ions travel through the ion passageway.

20. The hybrid ion mobility spectrometer of claim 15, further comprising:

an ion source coupled to an ion inlet of the single-pass drift tube, the ion source configured to generate ions from a sample, the generated ions entering the single-pass drift tube via the ion inlet thereof, and an ion detector to detect ions exiting an ion outlet of the single-pass drift tube and to produce an ion detection signal corresponding thereto.

* * * * *